US006989341B2

(12) United States Patent
Holtcamp et al.

(10) Patent No.: US 6,989,341 B2
(45) Date of Patent: *Jan. 24, 2006

(54) HALOGEN SUBSTITUTED CATALYST SYSTEM FOR OLEFIN POLYMERIZATION

(75) Inventors: Matthew W. Holtcamp, Huffman, TX (US); David A. Cano, Spring, TX (US)

(73) Assignee: Univation Technologies, LLC, Houston, TX (US)

( * ) Notice: Subject to any disclaimer, the term of this patent is extended or adjusted under 35 U.S.C. 154(b) by 8 days.

This patent is subject to a terminal disclaimer.

(21) Appl. No.: 10/602,579

(22) Filed: Jun. 24, 2003

(65) Prior Publication Data

US 2004/0127348 A1 Jul. 1, 2004

Related U.S. Application Data

(63) Continuation-in-part of application No. 10/058,571, filed on Jan. 28, 2002, now Pat. No. 6,841,504, and a continuation-in-part of application No. 10/186,361, filed on Jun. 28, 2002, now Pat. No. 6,703,338.

(51) Int. Cl.
B01J 31/00 (2006.01)
B01J 37/00 (2006.01)
C08F 4/02 (2006.01)
C08F 4/60 (2006.01)

(52) U.S. Cl. .................... 502/103; 502/117; 502/152; 502/155; 502/167

(58) Field of Classification Search ................ 502/102, 502/103, 117, 150, 152, 155, 167, 171
See application file for complete search history.

(56) References Cited

U.S. PATENT DOCUMENTS

| 4,377,699 | A | 3/1983 | Maurer ................... 548/469 |
| 6,147,173 | A | 11/2000 | Holtcamp .................. 526/133 |
| 6,211,105 | B1 | 4/2001 | Holtcamp .................. 502/103 |
| 6,239,062 | B1 | 5/2001 | Cribbs ..................... 502/167 |
| 6,608,224 | B2 * | 8/2003 | Resconi et al. ............. 556/27 |
| 2001/0025115 | A1 | 9/2001 | Campbell et al. ............. 556/7 |

FOREIGN PATENT DOCUMENTS

| EP | 0568151 A | 11/1993 |
| WO | WO 00/29454 | 5/2000 |
| WO | 01/27125 | 4/2001 |
| WO | WO 01/62764 | 8/2001 |
| WO | WO 02/102811 A | 12/2002 |
| WO | WO 03/64433 A | 8/2003 |

OTHER PUBLICATIONS

Abstract: Zheng, Ronghui et al., "*Modification effect of electron donors on supported catalyst for propylene polymerization*" retrieved from STN Database accession No. 108:38485 abstract & Shiyou Huagong, 16(10), 686-91 (1987).

Abstract: Kamaishi, Tadami et al., "*Catalyst for polymerization of .alpha.-olefins*" retrieved from STN Database accession No. 73:4358 abstract & JP 44 027734 B (Toyo Rayon Co., LTD) Nov. 17, 1969.

Abstract: Kamaishi, Tadami et al., "*Polymerization of .alpha.-olefin*" retrieved from STN Database accession No. 71:92059 abstract & JP 44 013148 B (Toyo Rayon Co., LTD) Jun. 12, 1969.

Abstract: Kamaishi, Tadami et al., "*Crystalline Polyolefins*" retrieved from STN Database accessiion No, 71:22482 abstract & JP 44 006828 B (Toyo Rayon Co., LTD) Mar. 25, 1969.

Abstract: Kamaishi, Tadami et al., "*Polypropylene*" retrieved from STN Database accession No. 70:88432 abstract & JP 43 029756 B (Toyo Rayon Co., LTD) Dec. 20, 1968.

Abstract: Kamaishi, Tadami et al., "*Polymerization of .alpha.-olefin*" retrieved from STN Database accession No. 70:68876 abstract & JP 43 018907 B (Toyo Rayon Co., LTD) Aug. 16, 1968.

Chen, Eugene You-Xian and Marks, Tobin, J.: "*Cocatalysts for Metal-Catalyzed Olefin Polymerization: Activators, Activation, Processes, and Structure—Activity Relationships*" Chemical Reviews vol. 100 No. 4, 1391-1434 (2000).

*Metallocene-based Polyolefins, Preparation, properties and Technology vol. One*, edited by J. Scheirs and W. Kaminsky, John Wiley and Sons Ltd., 8-9 (2000).

* cited by examiner

Primary Examiner—J. A. Lorengo
Assistant Examiner—J. Pasterczyk
(74) Attorney, Agent, or Firm—Kevin M. Faulkner

(57) ABSTRACT

A catalyst system is provided. In one aspect, the catalyst system includes one or more polymerization catalysts and at least one activator. The activator comprises one or more heterocyclic nitrogen-containing ligands coordinated to a Group 13 atom, wherein the activator is a reaction product of one or more alkyl substituted Group 13 atom-containing compounds and one or more heterocyclic nitrogen-containing compounds, the one or more heterocyclic nitrogen-containing ligands represented by:

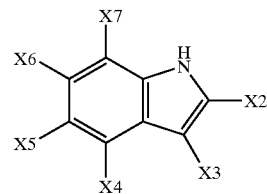

wherein each substituent X2, X3, X4, X5, X6, and X7 is independently selected from the group consisting of hydrogen, chlorine, fluorine, iodine, and bromine. The catalyst system may be supported or non-supported.

19 Claims, No Drawings

HALOGEN SUBSTITUTED CATALYST SYSTEM FOR OLEFIN POLYMERIZATION

CROSS-REFERENCE TO RELATED APPLICATIONS

This application is a continuation-in-part of Ser. No. 10/058,571, now U.S. Pat. No. 6,841,504, filed Jan. 28, 2002. This application is also a continuation-in-part of Ser. No. 10/186,361, now U.S. Pat. No. 6,703,338, filed Jun. 28, 2002.

BACKGROUND OF THE INVENTION

1. Field of the Invention

The present invention relates to polymerization catalyst activator compounds, to methods of making these activator compounds, to polymerization catalyst systems containing these activator compounds, and to polymerization processes utilizing the same. More specifically, the activators of the invention are the reaction product of a halogen substituted indole and a Group 13 atom-containing compound.

2. Description of the Related Art

Polymerization catalyst compounds are typically combined with an activator (or co-catalyst) to yield compositions having a vacant coordination site that will coordinate, insert, and polymerize olefins. Metallocene polymerization catalysts, for example, are typically activated with aluminoxanes which are generally oligomeric compounds containing —Al(R)—O— subunits, where R is an alkyl group. The most common alumoxane activator is methylalumoxane (MAO), produced by the hydrolysis of trimethylaluminum (TMA). MAO, however, is expensive to utilize because it must be added in great excess relative to the metallocene and because of the high cost of TMA. Additionally, MAO tends to be unstable as it precipitates out of solution over time.

As a result, alternative activators for metallocenes and other single-site polymerization catalysts have been discovered in recent years. For example, perfluorophenyl aluminum and borane complexes containing one anionic nitrogen-containing group have recently gained much attention.

Activator complexes having a Group 13 atom have also been suggested as a viable alternative to the expensive alumoxane activators. For example, U.S. Pat. Nos. 6,147,173 and 6,211,105 disclose a polymerization process and polymerization catalyst where the catalyst includes an activator complex having a Group 13 element and at least one halogenated, nitrogen-containing aromatic group ligand.

Each of these alternatives, including the formation of aluminoxane, require multi-step, complicated syntheses. There is a need, therefore, to provide a simpler method of cocatalyst synthesis and catalyst activation. There is also a need to improve catalyst economics by providing a highly active co-catalyst.

SUMMARY OF THE INVENTION

Embodiments of the invention include a catalyst system comprising one or more polymerization catalysts and at least one activator. In one aspect, the activator includes one or more heterocyclic nitrogen-containing ligands coordinated to a Group 13 atom, wherein the activator is a reaction product of one or more alkyl substituted Group 13 atom-containing compounds and one or more heterocyclic nitrogen-containing compounds, the one or more heterocyclic nitrogen-containing ligands represented by:

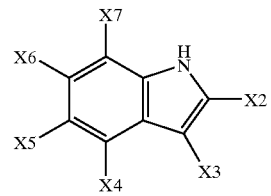

wherein each substituent X2, X3, X4, X5, X6, and X7 is independently selected from the group consisting of hydrogen, chlorine, fluorine, iodine, and bromine. The catalyst system may be supported or non-supported.

In another aspect, the activator is represented by one of the following formulas:

$$(R'_xM(JY)_y)_n \tag{a}$$

$$[((JY)_yR'_x)_nM—O—M((R'_x(JY)_y)_n]_m \tag{b}$$

$$(OMR'_x(JY)_y)_n \tag{c}$$

wherein M is a Group 13 atom, preferably aluminum or boron, and (JY) is a heterocyclic nitrogen-containing ligand represented by:

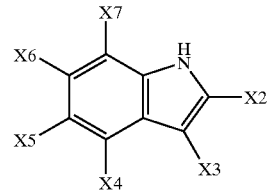

wherein each substituent X2, X3, X4, X5, X6, and X7 is independently selected from the group consisting of hydrogen, chlorine, fluorine, iodine, and bromine.

DETAILED DESCRIPTION OF THE PREFERRED EMBODIMENT

A catalyst system for olefin polymerization is provided. The catalyst system may be supported or non-supported and includes one or more catalysts and at least one activator. The activator is a reaction product of one or more Group 13 atom-containing compounds and one or more heterocyclic nitrogen-containing compounds. The heterocyclic compound includes 4 or more fused ring members and more preferably 5 or more fused ring members. At least one ring of the heterocyclic compound contains at least one atom selected from Group 15 or 16 of the Period Table of the Elements. Preferably, the ring of the heterocyclic compound includes at least one nitrogen, oxygen, and/or sulfur atom, and more preferably includes at least one nitrogen atom. Non-limiting examples of heterocyclic compounds include indole, carbazole, indoline, isoquinoline, isoindoline, quinaldine, quinoline, and quinoxaline. In a specific embodiment, the activator includes a mono-halogen substituted indole or a bi-halogen substituted indole. The halogen may be chlorine, iodine, bromine, fluorine, or any combination thereof. Preferably, the halogen is chlorine, bromine, fluorine, or any combination thereof.

The term "activator" as used herein refers to any compound or component, or combination of compounds or components, capable of enhancing the ability of a catalyst to polymerize olefin monomers to form polyolefins. The term "catalyst" is used interchangeably with the term "catalyst component", and includes any compound or component, or combination of compounds or components, that is capable of increasing the rate of a chemical reaction, such as the polymerization or oligomerization of one or more olefins. The term "catalyst system" as used herein includes at least one "catalyst" and at least one "activator". The "catalyst system" may also include other components, such as a support for example. The catalyst system may include any number of catalysts in any combination as described herein, as well as any activator in any combination as described herein.

As used herein, in reference to Periodic Table "Groups" of Elements, the "new" numbering scheme for the Periodic Table Groups are used as in the CRC HANDBOOK OF CHEMISTRY AND PHYSICS (David R. Lide ed., CRC Press 81$^{st}$ ed. 2000).

In a preferred embodiment, the activator includes one or more heterocyclic nitrogen-containing ligands coordinated to a Group 13 atom. The heterocyclic nitrogen-containing ligand is an indole represented by Formula (I).

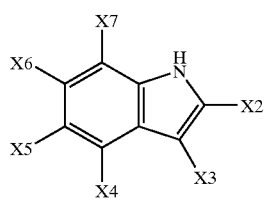

(I)

The indole includes substituents X2, X3, X4, X5, X6, and X7 located about the heterocyclic ring, as shown in Formula (I). Each substituent X2 to X7 is independently selected from hydrogen, halogens, alkyl groups, aryl groups, alkoxide groups, aryloxide groups, cyano groups, nitrous groups, sulfonyl groups, nitrile groups, phosphyl groups, and alkyl substituted aryl groups wherein each group may be halogenated or partially halogenated.

In one aspect, X4 is a halogen and X2, X3, X5–X7 are each hydrogen. In another aspect, X5 is a halogen and X2–X4, X6, and X7 are each hydrogen. In yet another aspect, X6 is a halogen and X2–X5 and X7 are each hydrogen. In still yet another aspect, both X5 and X6 are a halogen. The halogen may be chlorine, iodine, bromine, fluorine, or any combination thereof. Preferably, the halogen is chlorine, bromine, fluorine, or any combination thereof.

The one or more Group 13 atom-containing compounds preferably includes aluminum- or boron-containing compounds. For example, the Group 13 atom-containing compounds may include aluminoxane, modified aluminoxane, tri(n-butyl) ammonium tetrakis(pentafluorophenyl)boron, a trisperfluorophenyl boron metalloid precursor or a trisperfluoronapthyl boron metalloid precursor, polyhalogenated heteroborane anions, trimethylaluminum, triethylaluminum, triisobutylaluminum, tri-n-hexylaluminum, tri-n-octylaluminum, tris(2,2',2"-nona-fluorobiphenyl) fluoroaluminate, perchlorates, periodates, iodates and hydrates, (2,2'-bisphenyl-ditrimethylsilicate).4THF and organo-boron-aluminum compound, silylium salts and dioctadecylmethylammonium-bis(tris(pentafluorophenyl)borane)-benzimidazolide and combinations thereof.

In one aspect, the Group 13 atom-containing compound is an alkyl aluminum represented by the following formula (II):

wherein each R is independently a substituted or unsubstituted alkyl group and/or a substituted or unsubstituted aryl group. Preferably R is an alkyl group containing 1 to 30 carbon atoms. Some specific non-limiting examples of alkylaluminums include trimethylaluminum, triethylaluminum, triisobutylaluminum, tri-n-hexylaluminum, tri-n-octylaluminum, tri-iso-octylaluminum, triphenylaluminum, and combinations thereof.

In another aspect, the Group 13 atom-containing compound is an alumoxane. Preferred alumoxanes are oligomeric compounds containing —Al(R)—O— or —Al(R)$_2$—O— subunits, where R is an alkyl group. Examples of alumoxanes include methylalumoxane (MAO), modified methylalumoxane (MMAO), ethylalumoxane, triethylalumoxane, isobutylalumoxane, tetraethyldialumoxane and di-isobutylalumoxane. There are a variety of methods for preparing alumoxane and modified alumoxanes, such as the methods described in U.S. Pat. No. 4,542,199 and Chen and Marks, 100 Chem. Rev. 1391 (2000).

In yet another aspect, the Group 13 atom-containing compound is a boron-containing compound. Exemplary boron-containing compounds include organoboranes which include boron and one or more alkyl, aryl, or aralkyl groups. Some specific embodiments include substituted and unsubstituted trialkylboranes and triarylboranes, such as tris(pentafluorophenyl)borane, triphenylborane, tri-n-octylborane, and derivatives thereof, for example. These and other boron-containing compounds are described in U.S. Pat. Nos. 5,153,157; 5,198,401; and 5,241,025.

Preferably, the one or more Group 13 atom-containing compounds and the halogen substituted heterocyclic compounds of Formula (I) yield an activator represented by the following Formulas (III), (IV), or (V).

(III)

or

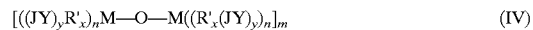

(IV)

or

(V)

In Formulas (III), (IV) and (V), M is a Group 13 atom, such as boron or aluminum. (JY) represents the heterocyclic group of Formula (I) and is associated with M, and preferably coordinated to M.

In Formula (III), n is 1 or 2. In Formula (IV) n is 2. In Formula (V) n is a number from 1 to 1000 preferably 1 to 100, more preferably 5 to 50, and even more preferably 5–25.

In Formula (IV), m is a number from 1 to 10.
In Formula (III), x+y=the valence of M.
In Formula (IV), x+y=the valence of M−1.
In Formula (V), x+y=valence of M−2.

Each R' is a substituent group bonded to M. Non-limiting examples of substituent R' groups include hydrogen, linear or branched alkyl radicals, linear or branched alkenyl radicals, linear or branched alkynyl radicals, cycloalkyl radicals, aryl radicals, acyl radicals, aroyl radicals, alkoxy radicals, aryloxy radicals, alkylthio radicals, dialkylamino radicals, alkoxycarbonyl radicals, aryloxycarbonyl radicals, carbamoyl radicals, alkyl radicals, dialkyl radicals, carbamoyl radicals, acyloxy radicals, acylamino radicals, aroylamino radicals, straight alkylene radicals, branched alkylene radicals, cyclic alkylene radicals, or any combination thereof.

More specific embodiments of R' include a methyl, ethyl, propyl, butyl, pentyl, hexyl, cyclopentyl, cyclohexyl, benzyl or phenyl group, including all their isomers, for example tertiary butyl, isopropyl, and the like. Other embodiments of R' include hydrocarbyl radicals such as fluoromethyl, fluoroethyl, difluoroethyl, iodopropyl, bromohexyl, chlorobenzyl; hydrocarbyl substituted organometalloid radicals including trimethylsilyl, trimethylgermyl, methyldiethylsilyl and the like; halocarbyl-substituted organometalloid radicals including tris(trifluoromethyl)silyl, methyl-bis(difluoromethyl)silyl, bromoethyldimethylgermyl and the like; disubstitiuted boron radicals including dimethylboron for example; disubstituted Group 15 radicals including dimethylamine, dimethylphosphine, diphenylamine, methylphenylphosphine; and Group 16 radicals including methoxy, ethoxy, propoxy, phenoxy, methylsulfide and ethylsulfide.

Further, each R' may include carbon, silicon, boron, aluminum, nitrogen, phosphorous, oxygen, tin, sulfur, or germanium atoms and the like. Still further, each R' may include olefins such as olefinically unsaturated substituents including vinyl-terminated ligands, such as but-3-enyl, prop-2-enyl, hex-5-enyl and the like, for example. Also, at least two R' groups, preferably two adjacent R' groups, may be joined to form a ring structure having from 3 to 30 atoms selected from carbon, nitrogen, oxygen, phosphorous, silicon, germanium, aluminum, boron, or a combination thereof. Also, a substituent group R' such as 1-butanyl may form a carbon sigma bond to the metal M.

Catalyst Compositions

The activators described above may be utilized in conjunction with any suitable polymerization catalyst to form an active polymerization catalyst system. Typically, the mole ratio of the metal of the activator to the metal of the catalyst composition is in the range of between 0.3:1 to 10,000:1, preferably 100:1 to 5000:1, and most preferably 500:1 to 2000:1. Exemplary polymerization catalysts include metallocene catalyst compositions, Group 15-containing metal catalyst compositions, and phenoxide transition metal catalyst compositions, which are discussed in more detail below.

Metallocene Catalyst Compositions

Metallocene catalyst compounds are generally described throughout in, for example, 1 & 2 METALLOCENE-BASED POLYOLEFINS (John Scheirs & W. Kaminsky eds., John Wiley & Sons, Ltd. 2000); G. G. Hlatky in 181 COORDINATION CHEM. REV. 243–296 (1999) and in particular, for use in the synthesis of polyethylene in 1 METALLOCENE-BASED POLYOLEFINS 261–377 (2000). The metallocene catalyst compounds as described herein include "half sandwich" and "full sandwich" compounds having one or more Cp ligands (cyclopentadienyl and ligands isolobal to cyclopentadienyl) bound to at least one Group 3 to Group 12 metal atom, and one or more leaving group(s) bound to the at least one metal atom. Hereinafter, these compounds will be referred to as "metallocenes" or "metallocene catalyst components". The metallocene catalyst component is supported on a support material in a particular embodiment as described further below, and may be supported with or without another catalyst component.

The Cp ligands are one or more rings or ring system(s), at least a portion of which includes π-bonded systems, such as cycloalkadienyl ligands and heterocyclic analogues. The ring(s) or ring system(s) typically comprise atoms selected from the group consisting of Groups 13 to 16 atoms, and more particularly, the atoms that make up the Cp ligands are selected from the group consisting of carbon, nitrogen, oxygen, silicon, sulfur, phosphorous, germanium, boron and aluminum and combinations thereof, wherein carbon makes up at least 50% of the ring members. Even more particularly, the Cp ligand(s) are selected from the group consisting of substituted and unsubstituted cyclopentadienyl ligands and ligands isolobal to cyclopentadienyl, non-limiting examples of which include cyclopentadienyl, indenyl, fluorenyl and other structures. Further non-limiting examples of such ligands include cyclopentadienyl, cyclopentaphenanthreneyl, indenyl, benzindenyl, fluorenyl, octahydrofluorenyl, cyclooctatetraenyl, cyclopentacyclododecene, phenanthrindenyl, 3,4-benzofluorenyl, 9-phenylfluorenyl, 8-H-cyclopent[a]acenaphthylenyl, 7H-dibenzofluorenyl, indeno[1,2-9]anthrene, thiophenoindenyl, thiophenofluorenyl, hydrogenated versions thereof (e.g., 4,5,6,7-tetrahydroindenyl, or "$H_4$Ind"), substituted versions thereof (as described in more detail below), and heterocyclic versions thereof.

The metal atom "M" of the metallocene catalyst compound, as described throughout the specification and claims, may be selected from the group consisting of Groups 3 through 12 atoms and lanthanide Group atoms in one embodiment; and selected from the group consisting of Groups 3 through 10 atoms in a more particular embodiment, and selected from the group consisting of Sc, Ti, Zr, Hf, V, Nb, Ta, Mn, Re, Fe, Ru, Os, Co, Rh, Ir, and Ni in yet a more particular embodiment; and selected from the group consisting of Groups 4, 5 and 6 atoms in yet a more particular embodiment, and a Ti, Zr, Hf atoms in yet a more particular embodiment, and Zr in yet a more particular embodiment. The oxidation state of the metal atom "M" may range from 0 to +7 in one embodiment; and in a more particular embodiment, is +1, +2, +3, +4 or +5; and in yet a more particular embodiment is +2, +3 or +4. The groups bound the metal atom "M" are such that the compounds described below in the formulas and structures are neutral, unless otherwise indicated. The Cp ligand(s) form at least one chemical bond with the metal atom M to form the "metallocene catalyst compound". The Cp ligands are distinct from the leaving groups bound to the catalyst compound in that they are not highly susceptible to substitution/abstraction reactions.

In one aspect, the one or more metallocene catalyst components are represented formula (VI):

$$Cp^A Cp^B MX_n \qquad\qquad\qquad (VI)$$

wherein M is as described above; each X is chemically bonded to M; each Cp group is chemically bonded to M; and n is 0 or an integer from 1 to 4, and either 1 or 2 in a particular embodiment.

The ligands represented by $Cp^A$ and $Cp^B$ in formula (VI) may be the same or different cyclopentadienyl ligands or ligands isolobal to cyclopentadienyl, either or both of which may contain heteroatoms and either or both of which may be substituted by a group R. In one embodiment, $Cp^A$ and $Cp^B$ are independently selected from the group consisting of cyclopentadienyl, indenyl, tetrahydroindenyl, fluorenyl, and substituted derivatives of each.

Independently, each $Cp^A$ and $Cp^B$ of formula (VI) may be unsubstituted or substituted with any one or combination of substituent groups R. Non-limiting examples of substituent groups R as used in structure (VI) include hydrogen radicals, alkyls, alkenyls, alkynyls, cycloalkyls, aryls, acyls, aroyls, alkoxys, aryloxys, alkylthiols, dialkylamines, alkylamidos, alkoxycarbonyls, aryloxycarbonyls, carbomoyls, alkyl- and dialkyl-carbamoyls, acyloxys, acylaminos, aroylaminos, and combinations thereof.

More particular non-limiting examples of alkyl substituents R associated with formula (VI) through (V) include methyl, ethyl, propyl, butyl, pentyl, hexyl, cyclopentyl, cyclohexyl, benzyl, phenyl, methylphenyl, and tert-butylphenyl groups and the like, including all their isomers, for example tertiary-butyl, isopropyl, and the like. Other possible radicals include substituted alkyls and aryls such as, for example, fluoromethyl, fluroethyl, difluoethyl, iodopropyl, bromohexyl, chlorobenzyl and hydrocarbyl substituted organometalloid radicals including trimethylsilyl, trimethylgermyl, methyldiethylsilyl and the like; and halocarbyl-substituted organometalloid radicals including tris(trifluoromethyl)silyl, methylbis(difluoromethyl)silyl, bromomethyldimethylgermyl and the like; and disubstituted boron radicals including dimethylboron for example; and disubstituted Group 15 radicals including dimethylamine, dimethylphosphine, diphenylamine, methylphenylphosphine, Group 16 radicals including methoxy, ethoxy, propoxy, phenoxy, methylsulfide and ethylsulfide. Other substituents R include olefins such as but not limited to olefinically unsaturated substituents including vinyl-terminated ligands, for example 3-butenyl, 2-propenyl, 5-hexenyl and the like. In one embodiment, at least two R groups, two adjacent R groups in one embodiment, are joined to form a ring structure having from 3 to 30 atoms selected from the group consisting of carbon, nitrogen, oxygen, phosphorous, silicon, germanium, aluminum, boron and combinations thereof. Also, a substituent group R group such as 1-butanyl may form a bonding association to the element M.

Each X in the formula (VI) above and for the formulas/structures (II) through (V) below is independently selected from the group consisting of: any leaving group in one embodiment; halogen ions, hydrides, $C_1$ to $C_{12}$ alkyls, $C_2$ to $C_{12}$ alkenyls, $C_6$ to $C_{12}$ aryls, $C_7$ to $C_{20}$ alkylaryls, $C_1$ to $C_{12}$ alkoxys, $C_6$ to $C_{16}$ aryloxys, $C_7$ to $C_{18}$ alkylaryloxys, $C_1$ to $C_{12}$ fluoroalkyls, $C_6$ to $C_{12}$ fluoroaryls, and $C_1$ to $C_{12}$ heteroatom-containing hydrocarbons and substituted derivatives thereof in a more particular embodiment; hydride, halogen ions, $C_1$ to $C_6$ alkyls, $C_2$ to $C_6$ alkenyls, $C_7$ to $C_{18}$ alkylaryls, $C_1$ to $C_6$ alkoxys, $C_6$ to $C_{14}$ aryloxys, $C_7$ to $C_{16}$ alkylaryloxys, $C_1$ to $C_6$ alkylcarboxylates, $C_1$ to $C_6$ fluorinated alkylcarboxylates, $C_6$ to $C_{12}$ arylcarboxylates, $C_7$ to $C_{18}$ alkylarylcarboxylates, $C_1$ to $C_6$ fluoroalkyls, $C_2$ to $C_6$ fluoroalkenyls, and $C_7$ to $C_{18}$ fluoroalkylaryls in yet a more particular embodiment; hydride, chloride, fluoride, methyl, phenyl, phenoxy, benzoxy, tosyl, fluoromethyls and fluorophenyls in yet a more particular embodiment; $C_1$ to $C_{12}$ alkyls, $C_2$ to $C_{12}$ alkenyls, $C_6$ to $C_{12}$ aryls, $C_7$ to $C_{20}$ alkylaryls, substituted $C_1$ to $C_{12}$ alkyls, substituted $C_6$ to $C_{12}$ aryls, substituted $C_7$ to $C_{20}$ alkylaryls and $C_1$ to $C_{12}$ heteroatom-containing alkyls, $C_1$ to $C_{12}$ heteroatom-containing aryls and $C_1$ to $C_{12}$ heteroatom-containing alkylaryls in yet a more particular embodiment; chloride, fluoride, $C_1$ to $C_6$ alkyls, $C_2$ to $C_6$ alkenyls, $C_7$ to $C_{18}$ alkylaryls, halogenated $C_1$ to $C_6$ alkyls, halogenated $C_2$ to $C_6$ alkenyls, and halogenated $C_7$ to $C_{18}$ alkylaryls in yet a more particular embodiment; fluoride, methyl, ethyl, propyl, phenyl, methylphenyl, dimethylphenyl, trimethylphenyl, fluoromethyls (mono-, di- and trifluoromethyls) and fluorophenyls (mono-, di-, tri-, tetra- and pentafluorophenyls) in yet a more particular embodiment.

Other non-limiting examples of X groups in formula (VI) include amines, phosphines, ethers, carboxylates, dienes, hydrocarbon radicals having from 1 to 20 carbon atoms, fluorinated hydrocarbon radicals (e.g., —$C_6F_5$ (pentafluorophenyl)), fluorinated alkylcarboxylates (e.g., $CF_3C(O)O^-$), hydrides and halogen ions and combinations thereof. Other examples of X ligands include alkyl groups such as cyclobutyl, cyclohexyl, methyl, heptyl, tolyl, trifluoromethyl, tetramethylene, pentamethylene, methylidene, methyoxy, ethyoxy, propoxy, phenoxy, bis(N-methylanilide), dimethylamide, dimethylphosphide radicals and the like. In one embodiment, two or more X's form a part of a fused ring or ring system.

In another aspect, the metallocene catalyst component includes those of formula (VI) where $Cp^A$ and $Cp^B$ are bridged to each other by at least one bridging group, (A), such that the structure is represented by formula (VII):

$$Cp^A(A)Cp^B MX_n \qquad (VII)$$

These bridged compounds represented by formula (VII) are known as "bridged metallocenes". $Cp^A$, $Cp^B$, M, X and n in structure (VII) are as defined above for formula (VI); and wherein each Cp ligand is chemically bonded to M, and (A) is chemically bonded to each Cp. Non-limiting examples of bridging group (A) include divalent hydrocarbon groups containing at least one Group 13 to 16 atom, such as but not limited to at least one of a carbon, oxygen, nitrogen, silicon, aluminum, boron, germanium and tin atom and combinations thereof; wherein the heteroatom may also be $C_1$ to $C_{12}$ alkyl or aryl substituted to satisfy neutral valency. The bridging group (A) may also contain substituent groups R as defined above (for formula (VI)) including halogen radicals and iron. More particular non-limiting examples of bridging group (A) are represented by $C_1$ to $C_6$ alkylenes, substituted $C_1$ to $C_6$ alkylenes, oxygen, sulfur, $R'_2C=$, $R'_2Si=$, $—Si(R')_2Si(R'_2)—$, $R'_2Ge=$, $R'P=$ (wherein "=" represents two chemical bonds), where R' is independently selected from the group consisting of hydride, hydrocarbyl, substituted hydrocarbyl, halocarbyl, substituted halocarbyl, hydrocarbyl-substituted organometalloid, halocarbyl-substituted organometalloid, disubstituted boron, disubstituted Group 15 atoms, substituted Group 16 atoms, and halogen radical; and wherein two or more R' may be joined to form a ring or ring system. In one embodiment, the bridged metallocene catalyst component of formula (VII) has two or more bridging groups (A).

Other non-limiting examples of bridging group (A) include methylene, ethylene, ethylidene, propylidene, isopropylidene, diphenylmethylene, 1,2-dimethylethylene, 1,2-diphenylethylene, 1,1,2,2-tetramethylethylene, dimethylsilyl, diethylsilyl, methyl-ethylsilyl, trifluoromethylbutylsilyl, bis(trifluoromethyl)silyl, di(n-butyl)silyl, di(n-propyl)silyl, di(i-propyl)silyl, di(n-hexyl)silyl, dicyclohexylsilyl, diphenylsilyl, cyclohexylphenylsilyl, t-butylcyclohexylsilyl, di(t-butylphenyl)silyl, di(p-tolyl)silyl and the corresponding moieties wherein the Si atom is replaced by a Ge or a C atom; dimethylsilyl, diethylsilyl, dimethylgermyl and diethylgermyl.

In another embodiment, bridging group (A) may also be cyclic, comprising, for example 4 to 10, 5 to 7 ring members in a more particular embodiment. The ring members may be selected from the elements mentioned above, from one or more of B, C, Si, Ge, N and O in a particular embodiment. Non-limiting examples of ring structures which may be present as or part of the bridging moiety are cyclobutylidene, cyclopentylidene, cyclohexylidene, cycloheptylidene, cyclooctylidene and the corresponding rings where one or two carbon atoms are replaced by at least one of Si, Ge, N and O, in particular, Si and Ge. The bonding arrangement between the ring and the Cp groups may be either cis-, trans-, or a combination.

The cyclic bridging groups (A) may be saturated or unsaturated and/or carry one or more substituents and/or be fused to one or more other ring structures. If present, the one or more substituents are selected from the group consisting of hydrocarbyl (e.g., alkyl such as methyl) and halogen (e.g., F, Cl) in one embodiment. The one or more Cp groups which the above cyclic bridging moieties may optionally be fused to may be saturated or unsaturated and are selected from the group consisting of those having 4 to 10, more particularly 5, 6 or 7 ring members (selected from the group consisting of C, N, O and S in a particular embodiment) such as, for example, cyclopentyl, cyclohexyl and phenyl. Moreover, these ring structures may themselves be fused such as, for example, in the case of a naphthyl group. Moreover, these (optionally fused) ring structures may carry one or more substituents. Illustrative, non-limiting examples of these substituents are hydrocarbyl (particularly alkyl) groups and halogen atoms.

The ligands $Cp^A$ and $Cp^B$ of formulae (VI) and (VII) are different from each other in one embodiment, and the same in another embodiment.

In yet another aspect, the metallocene catalyst components include mono-ligand metallocene compounds (e.g., mono cyclopentadienyl catalyst components) such as described in WO 93/08221 for example. In this embodiment, the at least one metallocene catalyst component is a bridged "half-sandwich" metallocene represented by the formula (VIII):

$$Cp^A(A)QMX_n \qquad (VIII)$$

wherein $Cp^A$ is defined above and is bound to M; (A) is a bridging group bonded to Q and $Cp^A$; and wherein an atom from the Q group is bonded to M; and n is 0 or an integer from 1 to 3; 1 or 2 in a particular embodiment. In formula (VIII) above, $Cp^A$, (A) and Q may form a fused ring system. The X groups and n of formula (VIII) are as defined above in formula (VI) and (VII). In one embodiment, $Cp^A$ is selected from the group consisting of cyclopentadienyl, indenyl, tetrahydroindenyl, fluorenyl, substituted versions thereof, and combinations thereof.

In formula (VIII), Q is a heteroatom-containing ligand in which the bonding atom (the atom that is bonded with the metal M) is selected from the group consisting of Group 15 atoms and Group 16 atoms in one embodiment, and selected from the group consisting of nitrogen, phosphorus, oxygen or sulfur atom in a more particular embodiment, and nitrogen and oxygen in yet a more particular embodiment. Non-limiting examples of Q groups include alkylamines, arylamines, mercapto compounds, ethoxy compounds, carboxylates (e.g., pivalate), carbamates, azenyl, azulene, pentalene, phosphoyl, phosphinimine, pyrrolyl, pyrozolyl, carbazolyl, borabenzene other compounds comprising Group 15 and Group 16 atoms capable of bonding with M.

In yet another aspect, the at least one metallocene catalyst component is an unbridged "half sandwich" metallocene represented by the formula (IX):

$$Cp^A MQ_q X_n \qquad (IX)$$

wherein $Cp^A$ is defined as for the Cp groups in (VI) and is a ligand that is bonded to M; each Q is independently bonded to M; Q is also bound to $Cp^A$ in one embodiment; X is a leaving group as described above in (VI); n ranges from 0 to 3, and is 1 or 2 in one embodiment; q ranges from 0 to 3, and is 1 or 2 in one embodiment. In one embodiment, $Cp^A$ is selected from the group consisting of cyclopentadienyl, indenyl, tetrahydroindenyl, fluorenyl, substituted version thereof, and combinations thereof.

In formula (IX), Q is selected from the group consisting of ROO⁻, RO—, R(O)—, —NR—, —CR$_2$—, —S—, —NR$_2$, —CR$_3$, —SR, —SiR$_3$, —PR$_2$, —H, and substituted and unsubstituted aryl groups, wherein R is selected from the group consisting of $C_1$ to $C_6$ alkyls, $C_6$ to $C_{12}$ aryls, $C_1$ to $C_6$ alkylamines, $C_6$ to $C_{12}$ alkylarylamines, $C_1$ to $C_6$ alkoxys, $C_6$ to $C_{12}$ aryloxys, and the like. Non-limiting examples of Q include $C_1$ to $C_{12}$ carbamates, $C_1$ to $C_{12}$ carboxylates (e.g., pivalate), $C_2$ to $C_{20}$ allyls, and $C_2$ to $C_{20}$ heteroallyl moieties.

Described another way, the "half sandwich" metallocenes above can be described as in formula (X), such as described in, for example, U.S. Pat. No. 6,069,213:

$$Cp^A M(Q_2 GZ)X_n \text{ or } T(Cp^A M(Q_2 GZ)X_n)_m \qquad (X)$$

wherein M, $Cp^A$, X and n are as defined above;

$Q_2 GZ$ forms a polydentate ligand unit (e.g., pivalate), wherein at least one of the Q groups form a bond with M, and is defined such that each Q is independently selected from the group consisting of —O—, —NR—, —CR$_2$— and —S—; G is either carbon or silicon; and Z is selected from the group consisting of R, —OR, —NR$_2$, —CR$_3$, —SR, —SiR$_3$, —PR$_2$, and hydride, providing that when Q is —NR—, then Z is selected from the group consisting of —OR, —NR$_2$, —SR, —SiR$_3$, —PR$_2$; and provided that neutral valency for Q is satisfied by Z; and wherein each R is independently selected from the group consisting of $C_1$ to $C_{10}$ heteroatom containing groups, $C_1$ to $C_{10}$ alkyls, $C_6$ to $C_{12}$ aryls, $C_6$ to $C_{12}$ alkylaryls, $C_1$ to $C_{10}$ alkoxys, and $C_6$ to $C_{12}$ aryloxys;

n is 1 or 2 in a particular embodiment; and

T is a bridging group selected from the group consisting of $C_1$ to $C_{10}$ alkylenes, $C_6$ to $C_{12}$ arylenes and $C_1$ to $C_{10}$ heteroatom containing groups, and $C_6$ to $C_{12}$ heterocyclic groups; wherein each T group bridges adjacent "$Cp^A M (Q_2 GZ)X_n$" groups, and is chemically bonded to the $Cp^A$ groups.

m is an integer from 1 to 7; m is an integer from 2 to 6 in a more particular embodiment.

In another aspect, the at least one metallocene catalyst component can be described more particularly in structures (XIa), (XIb), (XIc), (XId) (XIe) and (XIf):

(XIa-i)

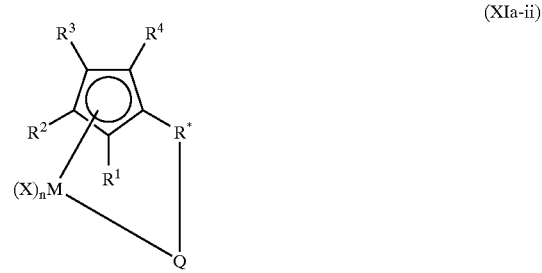

(XIa-ii)

-continued

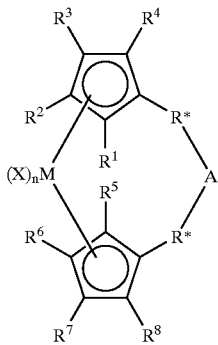
(XIb)

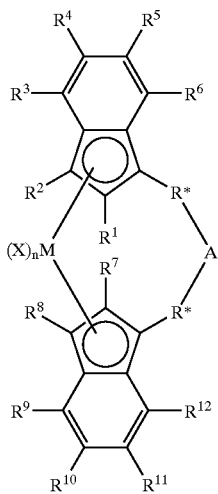
(XIc)

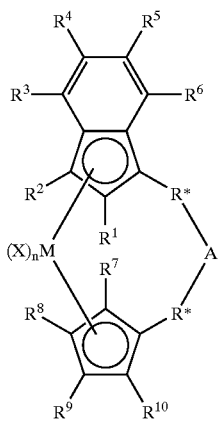
(XId)

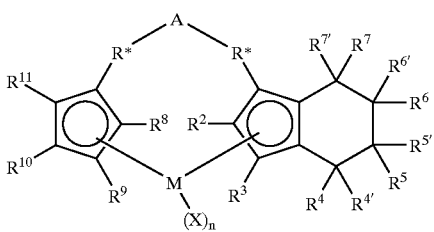
(XIe)

-continued

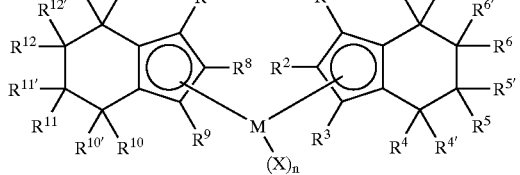
(XIf)

wherein in structures (XIa) to (XIf) M is selected from the group consisting of Group 3 to Group 12 atoms, and selected from the group consisting of Group 3 to Group 10 atoms in a more particular embodiment, and selected from the group consisting of Group 3 to Group 6 atoms in yet a more particular embodiment, and selected from the group consisting of Group 4 atoms in yet a more particular embodiment, and selected from the group consisting of Zr and Hf in yet a more particular embodiment; and is Zr in yet a more particular embodiment;

wherein Q in (XIa) to (XIf) is selected from the group consisting of alkylenes, aryls, arylenes, alkoxys, aryloxys, amines, arylamines (e.g., pyridyl) alkylamines, phosphines, alkylphosphines, substituted alkyls, substituted aryls, substituted alkoxys, substituted aryloxys, substituted amines, substituted alkylamines, substituted phosphines, substituted alkylphosphines, carbamates, heteroallyls, carboxylates (non-limiting examples of suitable carbamates and carboxylates include trimethylacetate, trimethylacetate, methylacetate, p-toluate, benzoate, diethylcarbamate, and dimethylcarbamate), fluorinated alkyls, fluorinated aryls, and fluorinated alkylcarboxylates; wherein the saturated groups defining Q comprise from 1 to 20 carbon atoms in one embodiment; and wherein the aromatic groups comprise from 5 to 20 carbon atoms in one embodiment;

wherein each R* is independently: selected from the group consisting of hydrocarbylenes and heteroatom-containing hydrocarbylenes in one embodiment; and selected from the group consisting of alkylenes, substituted alkylenes and heteroatom-containing hydrocarbylenes in another embodiment; and selected from the group consisting of $C_1$ to $C_{12}$ alkylenes, $C_1$ to $C_{12}$ substituted alkylenes, and $C_1$ to $C_{12}$ heteroatom-containing hydrocarbylenes in a more particular embodiment; and selected from the group consisting of $C_1$ to $C_4$ alkylenes in yet a more particular embodiment; and wherein both R* groups are identical in another embodiment in structures (XIf);

A is as described above for (A) in structure (VII), and more particularly, selected from the group consisting of a chemical bond, —O—, —S—, —SO$_2$—, —NR—, =SiR$_2$, =GeR$_2$, =SnR$_2$, —R$_2$SiSiR$_2$—, RP=, $C_1$ to $C_{12}$ alkylenes, substituted $C_1$ to $C_{12}$ alkylenes, divalent $C_4$ to $C_{12}$ cyclic hydrocarbons and substituted and unsubstituted aryl groups in one embodiment; and selected from the group consisting of $C_5$ to $C_8$ cyclic hydrocarbons, —CH$_2$CH$_2$—, =CR$_2$ and =SiR$_2$ in a more particular embodiment; wherein and R is selected from the group consisting of alkyls, cycloalkyls, aryls, alkoxys, fluoroalkyls and heteroatom-containing hydrocarbons in one embodiment; and R is selected from the group consisting of $C_1$ to $C_6$ alkyls, substituted phenyls, phenyl, and $C_1$ to $C_6$ alkoxys in a more particular embodiment; and R is selected from the group consisting of methoxy, methyl, phenoxy, and phenyl in yet a more particular embodiment;

wherein A may be absent in yet another embodiment, in which case each R* is defined as for $R^1$–$R^{13}$;

each X is as described above in (VI);

n is an integer from 0 to 4, and from 1 to 3 in another embodiment, and 1 or 2 in yet another embodiment; and $R^1$ through $R^{13}$ are independently: selected from the group consisting of hydrogen radical, halogen radicals, $C_1$ to $C_{12}$ alkyls, $C_2$ to $C_{12}$ alkenyls, $C_6$ to $C_{12}$ aryls, $C_7$ to $C_{20}$ alkylaryls, $C_1$ to $C_{12}$ alkoxys, $C_1$ to $C_{12}$ fluoroalkyls, $C_6$ to $C_{12}$ fluoroaryls, and $C_1$ to $C_{12}$ heteroatom-containing hydrocarbons and substituted derivatives thereof in one embodiment; selected from the group consisting of hydrogen radical, fluorine radical, chlorine radical, bromine radical, $C_1$ to $C_6$ alkyls, $C_2$ to $C_6$ alkenyls, $C_7$ to $C_{18}$ alkylaryls, $C_1$ to $C_6$ fluoroalkyls, $C_2$ to $C_6$ fluoroalkenyls, $C_7$ to $C_{18}$ fluoroalkylaryls in a more particular embodiment; and hydrogen radical, fluorine radical, chlorine radical, methyl, ethyl, propyl, isopropyl, butyl, isobutyl, tertiary butyl, hexyl, phenyl, 2,6-di-methylpheyl, and 4-tertiarbutylpheyl groups in yet a more particular embodiment; wherein adjacent R groups may form a ring, either saturated, partially saturated, or completely saturated.

The structure of the metallocene catalyst component represented by (XIa) may take on many forms such as disclosed in, for example, U.S. Pat. Nos. 5,026,798, 5,703, 187, and 5,747,406, including a dimer or oligomeric structure, such as disclosed in, for example, U.S. Pat. Nos. 5,026,798 and 6,069,213.

In a particular embodiment of the metallocene represented in (XId), $R^1$ and $R^2$ form a conjugated 6-membered carbon ring system that may or may not be substituted.

Non-limiting examples of metallocene catalyst components consistent with the description herein include:

cyclopentadienylzirconium $X_n$,
indenylzirconium $X_n$,
(1-methylindenyl)zirconium $X_n$,
(2-methylindenyl)zirconium $X_n$,
(1-propylindenyl)zirconium $X_n$,
(2-propylindenyl)zirconium $X_n$,
(1-butylindenyl)zirconium $X_n$,
(2-butylindenyl)zirconium $X_n$,
(methylcyclopentadienyl)zirconium $X_n$,
tetrahydroindenylzirconium $X_n$,
(pentamethylcyclopentadienyl)zirconium $X_n$,
cyclopentadienylzirconium $X_n$,
pentamethylcyclopentadienyltitanium $X_n$,
tetramethylcyclopentyltitanium $X_n$,
1,2,4-trimethylcyclopentadienylzirconium $X_n$,
dimethylsilyl(1,2,3,4-tetramethylcyclopentadienyl)(cyclopentadienyl)zirconium $X_n$,
dimethylsilyl(1,2,3,4-tetramethylcyclopentadienyl)(1,2,3-trimethylcyclopentadienyl)zirconium $X_n$,
dimethylsilyl(1,2,3,4-tetramethylcyclopentadienyl)(1,2-dimethylcyclopentadienyl)zirconium $X_n$,
dimethylsilyl(1,2,3,4-tetramethylcyclopentadienyl)(2-methylcyclopentadienyl)zirconium $X_n$,
dimethylsilyl(cyclopentadienyl)(indenyl)zirconium $X_n$,
dimethylsilyl(2-methylindenyl)(fluorenyl)zirconium $X_n$,
diphenylsilyl(1,2,3,4-tetramethyl-cyclopentadienyl)(3-propylcyclopentadienyl)zirconium $X_n$,
dimethylsilyl (1,2,3,4-tetramethylcyclopentadienyl)(3-t-butylcyclopentadienyl)zirconium $X_n$,
dimethylgermyl(1,2,3,4-dimethylcyclopentadienyl)(3-isopropylcyclopentadienyl)zirconium $X_n$,
dimethylsilyl(1,2,3,4-tetramethyl-cyclopentadienyl)(3-methylcyclopentadienyl)zirconium $X_n$,
diphenylmethylidene(cyclopentadienyl)(9-fluorenyl)zirconium $X_n$,
diphenylmethylidene(cyclopentadienyl)(indenyl)zirconium $X_n$,
iso-propylidenebis(cyclopentadienyl)zirconium $X_n$,
iso-propylidene(cyclopentadienyl)(9-fluorenyl)zirconium $X_n$,
iso-propylidene(3-methylcyclopentadienyl)(9-fluorenyl) zirconium $X_n$,
ethylenebis(9-fluorenyl)zirconium $X_n$,
meso-ethylenebis(1-indenyl)zirconium $X_n$,
ethylenebis(1-indenyl)zirconium $X_n$,
ethylenebis(2-methyl-1-indenyl)zirconium $X_n$,
ethylenebis(2-methyl-4,5,6,7-tetrahydro-1-indenyl)zirconium $X_n$,
ethylenebis(2-propyl-4,5,6,7-tetrahydro-1-indenyl)zirconium $X_n$,
ethylenebis(2-isopropyl-4,5,6,7-tetrahydro-1-indenyl)zirconium $X_n$,
ethylenebis(2-butyl-4,5,6,7-tetrahydro-1-indenyl)zirconium $X_n$,
ethylenebis(2-isobutyl-4,5,6,7-tetrahydro-1-indenyl)zirconium $X_n$,
dimethylsilyl(4,5,6,7-tetrahydro-1-indenyl)zirconium $X_n$,
diphenyl(4,5,6,7-tetrahydro-1-indenyl)zirconium $X_n$,
ethylenebis(4,5,6,7-tetrahydro-1-indenyl)zirconium $X_n$,
dimethylsilylbis(cyclopentadienyl)zirconium $X_n$,
dimethylsilylbis(9-fluorenyl)zirconium $X_n$,
dimethylsilylbis(1-indenyl)zirconium $X_n$,
dimethylsilylbis(2-methylindenyl)zirconium $X_n$,
dimethylsilylbis(2-propylindenyl)zirconium $X_n$,
dimethylsilylbis(2-butylindenyl)zirconium $X_n$,
diphenylsilylbis(2-methylindenyl)zirconium $X_n$,
diphenylsilylbis(2-propylindenyl)zirconium $X_n$,
diphenylsilylbis(2-butylindenyl)zirconium $X_n$,
dimethylgermylbis(2-methylindenyl)zirconium $X_n$
dimethylsilylbis(tetrahydroindenyl)zirconium $X_n$,
dimethylsilylbis(tetramethylcyclopentadienyl)zirconium $X_n$,
dimethylsilyl(cyclopentadienyl)(9-fluorenyl)zirconium $X_n$,
diphenylsilyl(cyclopentadienyl)(9-fluorenyl)zirconium $X_n$,
diphenylsilylbis(indenyl)zirconium $X_n$,
cyclotrimethylenesilyl(tetramethylcyclopentadienyl)(cyclopentadienyl)zirconium $X_n$,
cyclotetramethylenesilyl(tetramethylcyclopentadienyl) (cyclopentadienyl)zirconium $X_n$,
cyclotrimethylenesilyl(tetramethylcyclopentadienyl)(2-methylindenyl)zirconium $X_n$,
cyclotrimethylenesilyl(tetramethylcyclopentadienyl)(3-methylcyclopentadienyl)zirconium $X_n$,
cyclotrimethylenesilylbis(2-methylindenyl)zirconium $X_n$,
cyclotrimethylenesilyl(tetramethylcyclopentadienyl)(2,3,5-trimethylcyclopentadienyl)zirconium $X_n$,
cyclotrimethylenesilylbis(tetramethylcyclopentadienyl) zirconium $X_n$,
dimethylsilyl(tetramethylcyclopentadieneyl)(N-tert-butylamido)titanium $X_n$,
bis(cyclopentadienyl)chromium $X_n$,
bis(cyclopentadienyl)zirconium $X_n$,
bis(n-butylcyclopentadienyl)zirconium $X_n$,
bis(n-dodecylcyclopentadienyl)zirconium $X_n$,
bis(ethylcyclopentadienyl)zirconium $X_n$,
bis(iso-butylcyclopentadienyl)zirconium $X_n$, bis(iso-propylcyclopentadienyl)zirconium $X_n$,
bis(methylcyclopentadienyl)zirconium $X_n$,
bis(n-oxtylcyclopentadienyl)zirconium $X_n$,
bis(n-pentylcyclopentadienyl)zirconium $X_n$,
bis(n-propylcyclopentadienyl)zirconium $X_n$,
bis(trimethylsilylcyclopentadienyl)zirconium $X_n$,
bis(1,3-bis(trimethylsilyl)cyclopentadienyl)zirconium $X_n$,
bis(1-ethyl-2-methylcyclopentadienyl)zirconium $X_n$,
bis(1-ethyl-3-methylcyclopentadienyl)zirconium $X_n$,
bis(pentamethylcyclopentadienyl)zirconium $X_n$,
bis(pentamethylcyclopentadienyl)zirconium $X_n$,
bis(1-propyl-3-methylcyclopentadienyl)zirconium $X_n$,
bis(1-n-butyl-3-methylcyclopentadienyl)zirconium $X_n$,
bis(1-isobutyl-3-methylcyclopentadienyl)zirconium $X_n$,
bis(1-propyl-3-butylcyclopentadienyl)zirconium $X_n$,
bis(1,3-n-butylcyclopentadienyl)zirconium $X_n$,
bis(4,7-dimethylindenyl)zirconium $X_n$,
bis(indenyl)zirconium $X_n$,
bis(2-methylindenyl)zirconium $X_n$,
cyclopentadienylindenylzirconium $X_n$,
bis(n-propylcyclopentadienyl)hafnium $X_n$,
bis(n-butylcyclopentadienyl)hafnium $X_n$,
bis(n-pentylcyclopentadienyl)hafnium $X_n$,
(n-propyl cyclopentadienyl)(n-butyl cyclopentadienyl)hafnium $X_n$,
bis[(2-trimethylsilylethyl)cyclopentadienyl]hafnium $X_n$,
bis(trimethylsilyl cyclopentadienyl)hafnium $X_n$,
bis(2-n-propylindenyl)hafnium $X_n$,
bis(2-n-butylindenyl)hafnium $X_n$,
dimethylsilylbis(n-propylcyclopentadienyl)hafnium $X_n$,
dimethylsilylbis(n-butylcyclopentadienyl)hafnium $X_n$,
bis(9-n-propylfluorenyl)hafnium $X_n$,
bis(9-n-butylfluorenyl)hafnium $X_n$,
(9-n-propylfluorenyl)(2-n-propylindenyl)hafnium $X_n$,
bis(1-n-propyl-2-methylcyclopentadienyl)hafnium $X_n$,
(n-propylcyclopentadienyl)(1-n-propyl-3-n-butylcyclopentadienyl)hafnium $X_n$,
dimethylsilyl(tetramethylcyclopentadienyl)(cyclopropylamido)titanium $X_n$,
dimethylsilyl(tetramethyleyclopentadienyl)(cyclobutylamido)titanium $X_n$,
dimethylsilyl(tetramethyleyclopentadienyl)(cyclopentylamido)titanium $X_n$,
dimethylsilyl(tetramethylcyclopentadienyl)(cyclohexylamido)titanium $X_n$,
dimethylsilyl(tetramethylcyclopentadienyl)(cycloheptylamido)titanium $X_n$,
dimethylsilyl(tetramethylcyclopentadienyl)(cyclooctylamido)titanium $X_n$,
dimethylsilyl(tetramethylcyclopentadienyl)(cyclononylamido)titanium $X_n$,
dimethylsilyl(tetramethylcyclopentadienyl)(cyclodecylamido)titanium $X_n$,
dimethylsilyl(tetramethylcyclopentadienyl)(cycloundecylamido)titanium $X_n$,
dimethylsilyl(tetramethylcyclopentadienyl)(cyclododecylamido)titanium $X_n$,
dimethylsilyl(tetramethylcyclopentadienyl)(sec-butylamido)titanium $X_n$,
dimethylsilyl(tetramethylcyclopentadienyl)(n-octylamido)titanium $X_n$,
dimethylsilyl(tetramethylcyclopentadienyl)(n-decylamido)titanium $X_n$,
dimethylsilyl(tetramethylcyclopentadienyl)(n-octadecylamido)titanium $X_n$,
methylphenylsilyl(tetramethylcyclopentadienyl)(cyclopropylamido)titanium $X_n$,
methylphenylsilyl(tetramethylcyclopentadienyl)(cyclobutylamido)titanium $X_n$,
methylphenylsilyl(tetramethylcyclopentadienyl)(cyclopentylamido)titanium $X_n$,
methylphenylsilyl(tetramethylcyclopentadienyl)(cyclohexylamido)titanium $X_n$,
methylphenylsilyl(tetramethylcyclopentadienyl)(cycloheptylamido)titanium $X_n$,
methylphenylsilyl(tetramethylcyclopentadienyl)(cyclooctylamido)titanium $X_n$,
methylphenylsilyl(tetramethylcyclopentadienyl)(cyclononylamido)titanium $X_n$,
methylphenylsilyl(tetramethylcyclopentadienyl)(cyclodecylamido)titanium, $X_n$,
methylphenylsilyl(tetramethylcyclopentadienyl)(cycloundecylamido)titanium $X_n$,
methylphenylsilyl(tetramethylcyclopentadienyl)(cyclododecylamido)titanium $X_n$,
methylphenylsilyl(tetramethylcyclopentadienyl)(sec-butylamido)titanium $X_n$,
methylphenylsilyl(tetramethylcyclopentadienyl)(n-octylamido)titanium $X_n$,
methylphenylsilyl(tetramethylcyclopentadienyl)(n-decylamido)titanium $X_n$,
methylphenylsilyl(tetramethylcyclopentadienyl)(n-octadecylamido)titanium $X_n$,
diphenylsilyl(tetramethylcyclopentadienyl)(cyclopropylamido)titanium $X_n$,
diphenylsilyl(tetramethylcyclopentadienyl)(cyclobutylamido)titanium $X_n$,
diphenylsilyl(tetramethylcyclopentadienyl)(cyclopentylamido)titanium $X_n$,
diphenylsilyl(tetramethylcyclopentadienyl)(cyclohexylamido)titanium $X_n$,
diphenylsilyl(tetramethylcyclopentadienyl)(cycloheptylamido)titanium $X_n$,
diphenylsilyl(tetramethylcyclopentadienyl)(cyclooctylamido)titanium $X_n$,
diphenylsilyl(tetramethylcyclopentadienyl)(cyclononylamido)titanium $X_n$,
diphenylsilyl(tetramethylcyclopentadienyl)(cyclodecylamido)titanium $X_n$,
diphenylsilyl(tetramethylcyclopentadienyl)(cycloundecylamido)titanium $X_n$,
diphenylsilyl(tetramethylcyclopentadienyl)(cyclododecylamido)titanium $X_n$,
diphenylsilyl(tetramethylcyclopentadienyl)(sec-butylamido)titanium $X_n$,
diphenylsilyl(tetramethyleyclopentadienyl)(n-octylamido)titanium $X_n$,
diphenylsilyl(tetramethyleyclopentadienyl)(n-decylamido)titanium $X_n$,
diphenylsilyl(tetramethylcyclopentadienyl)(n-octadecylamido)titanium $X_n$,
and derivatives thereof.

By "derivatives thereof", it is meant any substitution or ring formation as described above in one embodiment; and in particular, replacement of the metal "M" (Cr, Zr, Ti or Hf) with an atom selected from the group consisting of Cr, Zr, Hf and Ti; and replacement of the "X" group with any of $C_1$ to $C_5$ alkyls, $C_6$ aryls, $C_6$ to $C_{10}$ alkylaryls, fluorine or chlorine; n is 1, 2 or 3.

It is contemplated that the metallocene catalysts components described above include their structural or optical or enantiomeric isomers (racemic mixture), and may be a pure enantiomer in one embodiment.

As used herein, a single, bridged, asymmetrically substituted metallocene catalyst component having a racemic and/or meso isomer does not, itself, constitute at least two different bridged, metallocene catalyst components.

The "metallocene catalyst component" may comprise any combination of any "embodiment" described herein.

Group 15-Containing Catalyst Compositions

"Group 15-containing catalyst components", as referred to herein, include Group 3 to Group 12 metal complexes, wherein the metal is 2 to 4 coordinate, the coordinating moiety or moieties including at least two Group 15 atoms, and up to four Group 15 atoms. In one embodiment, the Group 15-containing catalyst component is a complex of a Group 4 metal and from one to four ligands such that the Group 4 metal is at least 2 coordinate, the coordinating moiety or moieties including at least two nitrogens. Representative Group 15-containing compounds are disclosed in, for example, WO 98/46651, WO 99/01460; EP A1 0 893, 454; EP A1 0 894 005; U.S. Pat. Nos. 5,318,935; 5,889,128 6,333,389 B2 and 6,271,325 B1.

In one embodiment, the Group 15-containing catalyst components may include Group 4 imino-phenol complexes, Group 4 bis(amide) complexes, and Group 4 pyridyl-amide complexes that are active towards olefin polymerization to any extent.

The Group 15-containing catalyst component may be more particularly described by the following formula (XII):

$$\alpha_a\beta_b\gamma_g MX_n \quad (XII)$$

wherein β and γ are groups that each comprise at least one Group 14 to Group 16 atom; and β (when present) and γ are groups bonded to M through between 2 and 6 Group 14 to Group 16 atoms, at least two atoms being Group 15-containing atoms.

More particularly, β and γ are groups selected from Group 14 and Group 15-containing: alkyls, aryls, alkylaryls, and heterocyclic hydrocarbons, and chemically bonded combinations thereof in one embodiment; and selected from Group 14 and Group 15-containing: $C_1$ to $C_{10}$ alkyls, $C_6$ to $C_{12}$ aryls, $C_6$ to $C_{18}$ alkylaryls, and $C_4$ to $C_{12}$ heterocyclic hydrocarbons, and chemically bonded combinations thereof in a more particular embodiment; and selected from $C_1$ to $C_{10}$ alkylamines, $C_1$ to $C_{10}$ alkoxys, $C_6$ to $C_{20}$ alkylarylamines, $C_6$ to $C_{18}$ alkylaryloxys, and $C_4$ to $C_{12}$ nitrogen containing heterocyclic hydrocarbons, and $C_4$ to $C_{12}$ alkyl substituted nitrogen containing heterocyclic hydrocarbons and chemically bonded combinations thereof in yet a more particular embodiment; and selected from anilinyls, pyridyls, quinolyls, pyrrolyls, pyrimidyls, purinyls, imidazyls, indolyls, $C_1$ to $C_6$ alkyl substituted groups selected from anilinyls, pyridyls, quinolyls, pyrrolyls, pyrimidyls, purinyls, imidazyls, indolyls; $C_1$ to $C_6$ alkylamine substituted groups selected from anilinyls, pyridyls, quinolyls, pyrrolyls, pyrimidyls, purinyls, imidazyls, indolyls, amine substituted anilinyls, pyridyls, quinolyls, pyrrolyls, pyrimidyls, purinyls, imidazyls, and indolyls; hydroxy substituted groups selected from anilinyls, pyridyls, quinolyls, pyrrolyls, pyrimidyls, purinyls, imidazyls, and indolyls; methyl-substituted phenylamines, and chemically bonded combinations thereof in yet a more particular embodiment;

α is a linking (or "bridging") moiety that, when present, forms a chemical bond to each of β and γ, or two γ's, thus forming a "γαγ" or "γαβ" ligand bound to M; α may also comprise a Group 14 to Group 16 atom which may be bonded to M through the Group 14 to Group 16 atom in one embodiment; and more particularly, a is a divalent bridging group selected from alkylenes, arylenes, alkenylenes, heterocyclic arylenes, alkylarylenes, heteroatom containing alkylenes, heteroatom containing alkenylenes and heterocyclic hydrocarbonylenes in one embodiment; and selected from $C_1$ to $C_{10}$ alkylenes, $C_2$ to $C_{10}$ alkenylenes, $C_6$ to $C_{12}$ arylenes, $C_1$ to $C_{10}$ divalent ethers, $C_6$ to $C_{12}$ O- or N-containing arylenes, $C_2$ to $C_{10}$ alkyleneamines, $C_6$ to $C_{12}$ aryleneamines, and substituted derivatives thereof in yet a more particular embodiment;

a is an integer from 0 to 2; a is either 0 or 1 in a more particular embodiment; and a is 1 in yet a more particular embodiment; b is an integer from 0 to 2; g is an integer from 1 to 2; wherein in one embodiment, a is 1, b is 0 and g is 2; M is selected from Group 3 to Group 12 atoms in one embodiment; and selected from Group 3 to Group 10 atoms in a more particular embodiment; and selected from Group 3 to Group 6 atoms in yet a more particular embodiment; and selected from Ni, Cr, Ti, Zr and Hf in yet a more particular embodiment; and selected from Zr and Hf in yet a more particular embodiment; each X is as defined above; and n is an integer from 0 to 4 in one embodiment; and an integer from 1 to 3 in a more particular embodiment; and an integer from 2 to 3 in yet a more particular embodiment.

As used herein, "chemically bonded combinations thereof" means that adjacent groups, (β and γ groups) may form a chemical bond between them; in one embodiment, the β and γ groups are chemically bonded through one or more a groups there between.

As used herein, the terms "alkyleneamines", "aryleneamines", describe alkylamines and arylamines (respectively) that are deficient by two hydrogens, thus forming chemical bonds with two adjacent γ groups, or adjacent β and γ groups. Thus, an example of an alkyleneamine is —$CH_2CH_2N(CH_3)CH_2CH_2$—, and an example of a heterocyclic hydrocarbylene or aryleneamine is —$C_5H_3N$— (divalent pyridine). An "alkylene-arylamine" is a group such as, for example, —$CH_2CH_2(C_5H_3N)CH_2CH_2$—.

Described another way, the Group 15-containing catalyst component is represented by the structures (XIII) and (XIV):

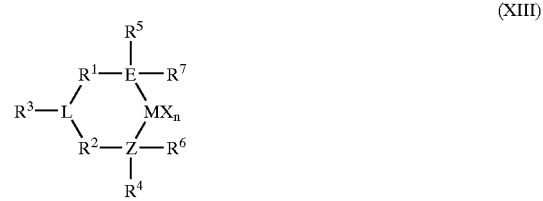

(XIII)

(XIV)

wherein E and Z are Group 15 elements independently selected from nitrogen and phosphorus in one embodiment; and nitrogen in a more particular embodiment;

L is selected from Group 15 atoms, Group 16 atoms, Group 15-containing hydrocarbylenes and a Group 16 containing hydrocarbylenes in one embodiment; wherein $R^3$ is absent when L is a Group 16 atom; in yet a more particular embodiment, when $R^3$ is absent, L is selected from heterocyclic hydrocarbylenes; and in yet a more particular embodiment, L is selected from nitrogen, phosphorous, anilinyls, pyridyls, quinolyls, pyrrolyls, pyrimidyls, purinyls, imidazyls, indolyls; $C_1$ to $C_6$ alkyl substituted groups selected from anilinyls, pyridyls, quinolyls, pyrrolyls, pyrimidyls, purinyls, imidazyls, and indolyls; $C_1$ to $C_6$ alkylamine substituted groups selected from anilinyls, pyridyls, quinolyls, pyrrolyls, pyrimidyls, purinyls, imidazyls, indolyls; amine substituted anilinyls, pyridyls, quinolyls, pyrrolyls, pyrimidyls, purinyls, imidazyls, and indolyls; hydroxy substituted groups selected from anilinyls, pyridyls, quinolyls, pyrrolyls, pyrimidyls, purinyls, imidazyls, and indolyls; methyl-substituted phenylamines, substituted derivatives thereof, and chemically bonded combinations thereof;

L' is selected from Group 15 atoms, Group 16 atoms, and Group 14 atoms in one embodiment; and selected from Group 15 and Group 16 atoms in a more particular embodiment; and is selected from groups as defined by L above in yet a more particular embodiment, wherein "EZL" and "EZL'" may be referred to as a "ligand", the EZL and EZL' ligands comprising the R* and $R^1$–$R^7$ groups;

wherein L and L' may or may not form a bond with M; y is an integer ranging from 0 to 2 (when y is 0, group L', *R and $R^3$ are absent);

M is selected from Group 3 to Group 5 atoms, Group 4 atoms in a more particular embodiment, and selected from Zr and Hf in yet a more particular embodiment;

n is an integer ranging from 1 to 4 in one embodiment; n is an integer ranging from 2 to 3 in a more particular embodiment;

each X is as defined above;

$R^1$ and $R^2$ are independently: divalent bridging groups selected from alkylenes, arylenes, heteroatom containing alkylenes, heteroatom containing arylenes, substituted alkylenes, substituted arylenes and substituted heteroatom containing alkylenes, wherein the heteroatom is selected from silicon, oxygen, nitrogen, germanium, phosphorous, boron and sulfur in one embodiment; selected from $C_1$ to $C_{20}$ alkylenes, $C_6$ to $C_{12}$ arylenes, heteroatom-containing $C_1$ to $C_{20}$ alkylenes and heteroatom-containing $C_6$ to $C_{12}$ arylenes in a more particular embodiment; and in yet a more particular embodiment selected from —$CH_2$—, —$C(CH_3)_2$—, —$C(C_6H_5)_2$—, —$CH_2CH_2$—, —$CH_2CH_2CH_2$—, —Si$(CH_3)_2$—, —Si$(C_6H_5)_2$—, —$C_6H_{10}$—, —$C_6H_4$—, and substituted derivatives thereof, the substitutions including $C_1$ to $C_4$ alkyls, phenyl, and halogen radicals;

$R^3$ is absent in one embodiment; a group selected from hydrocarbyl groups, hydrogen radical, halogen radicals, and heteroatom-containing groups in a more particular embodiment; and selected from linear alkyls, cyclic alkyls, and branched alkyls having 1 to 20 carbon atoms in yet a more particular embodiment;

*R is absent in one embodiment; a group selected from hydrogen radical, Group 14 atom containing groups, halogen radicals, and a heteroatom-containing groups in yet a more particular embodiment;

$R^4$ and $R^5$ are independently: groups selected from alkyls, aryls, substituted aryls, cyclic alkyls, substituted cyclic alkyls, cyclic arylalkyls, substituted cyclic arylalkyls and multiple ring systems in one embodiment, each group having up to 20 carbon atoms, and between 3 and 10 carbon atoms in a more particular embodiment; selected from $C_1$ to $C_{20}$ alkyls, $C_1$ to $C_{20}$ aryls, $C_1$ to $C_{20}$ arylalkyls, and heteroatom-containing groups (for example $PR_3$, where R is an alkyl group) in yet a more particular embodiment; and $R^6$ and $R^7$ are independently: absent in one embodiment; groups selected from hydrogen radicals, halogen radicals, heteroatom-containing groups and hydrocarbyls in a more particular embodiment; selected from linear, cyclic and branched alkyls having from 1 to 20 carbon atoms in yet a more particular embodiment;

wherein $R^1$ and $R^2$ may be associated with one another, and/or $R^4$ and $R^5$ may be associated with one another as through a chemical bond.

Described yet more particularly, the Group 15-containing catalyst component can be described as the embodiments shown in structures (IV), (V) and (VI) (where "N" is nitrogen):

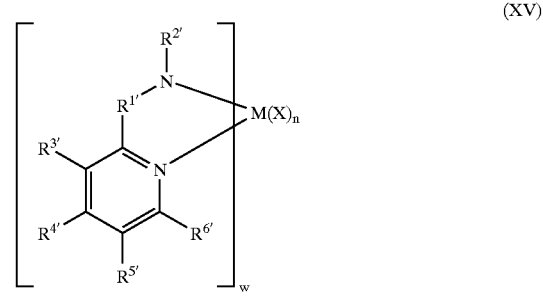

(XV)

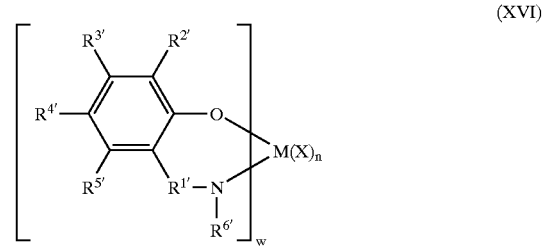

(XVI)

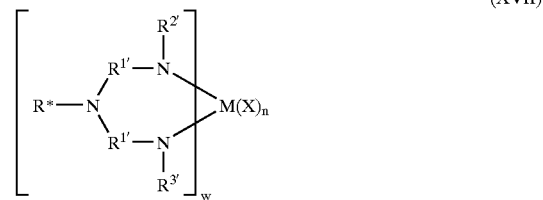

(XVII)

wherein structure (XV) represents pyridyl-amide structures, structure (XVI) represents imino-phenol structures, and structure (XVII) represents bis(amide) structures; wherein w is an integer from 1 to 3, and 1 or 2 in a more particular embodiment, and 1 in yet a more particular embodiment; M is a Group 3 to Group 13 element, a Group 3 to Group 6 element in a more particular embodiment, and a Group 4 element in yet a more particular embodiment; each X is independently selected from hydrogen radicals, halogen ions (desirably, anions of fluorine, chlorine, and bromine); $C_1$ to $C_6$ alkyls; $C_1$ to $C_6$ fluoroalkyls, $C_6$ to $C_{12}$ aryls; $C_6$ to $C_{12}$ fluoroalkyls, $C_1$ to $C_6$ alkoxys, $C_6$ to $C_{12}$ aryloxys, and $C_7$ to $C_{18}$ alkylaryloxys; n is an integer ranging from 0 to 4, and from 1 to 3 in a more particular embodiment, and from 2 to 3 in yet a more particular embodiment, and 2 in yet a more particular embodiment;

and further, wherein in structures (XV), (XVI) and (XVII), $R^{1'}$ is selected from hydrocarbylenes and heteroatom-containing hydrocarbylenes in one embodiment, and selected from —$SiR_2$—, alkylenes, arylenes, alkenylenes and substituted alkylenes, substituted alkenylenes and substituted arylenes in another embodiment; and selected from —SiR$_2$—, C$_1$ to C$_6$ alkylenes, C$_6$ to C$_{12}$ arylenes, C$_1$ to C$_6$ substituted alkylenes and C$_6$ to C$_{12}$ substituted arylenes in another embodiment, wherein R is selected from C$_1$ to C$_6$ alkyls and C$_6$ to C$_{12}$ aryls; and R$^{2'}$, R$^{3'}$, R$^{4'}$, R$^{5'}$, R$^{6'}$ and R* are independently selected from hydride, C$_1$ to C$_{10}$ alkyls, C$_6$ to C$_{12}$ aryls, C$_6$ to C$_{18}$ alkylaryls, C$_4$ to C$_{12}$ heterocyclic hydrocarbyls, substituted C$_1$ to C$_{10}$ alkyls, substituted C$_6$ to C$_{12}$ aryls, substituted C$_6$ to C$_{18}$ alkylaryls, and substituted C$_4$ to C$_{12}$ heterocyclic hydrocarbyls and chemically bonded combinations thereof in one embodiment; wherein R* is absent in a particular embodiment; and in another embodiment, R*—N represents a nitrogen containing group or ring such as a pyridyl group or a substituted pyridyl group that is bridged by the R$^{1'}$ groups. In yet another embodiment, R*—N is absent, and the R$^{1'}$ groups form a chemical bond to one another.

In one embodiment of structures (XV), (XVI) and (XVII), R$^{1'}$ is selected from methylene, ethylene, 1-propylene, 2-propylene, =Si(CH$_3$)$_2$, =Si(phenyl)$_2$, —CH=, —C(CH$_3$)=, —C(phenyl)$_2$—, —C(phenyl)= (wherein "=" represents two chemical bonds), and the like.

In a particular embodiment of structure (XVI), R$^{2'}$ and R$^{4'}$ are selected from 2-methylphenyl, 2-n-propylphenyl, 2-iso-propylphenyl, 2-iso-butylphenyl, 2-tert-butylphenyl, 2-fluorophenyl, 2-chlorophenyl, 2-bromophenyl, 2-methyl-4-chlorophenyl, 2-n-propyl-4-chlorophenyl, 2-iso-propyl-4-chlorophenyl, 2-iso-butyl-4-chlorophenyl, 2-tert-butyl-4-chlorophenyl, 2-methyl-4-fluorophenyl, 2-n-propyl-4-fluorophenyl, 2-iso-propyl-4-fluorophenyl, 2-iso-butyl-4-fluorophenyl, 2-tert-butyl-4-fluorophenyl, 2-methyl-4-bromophenyl, 2-n-propyl-4-bromophenyl, 2-iso-propyl-4-bromophenyl, 2-iso-butyl-4-bromophenyl, 2-tert-butyl-4-bromophenyl, and the like.

In yet another particular embodiment of structures (XV) and (XVII), R$^{2'}$ and R$^{3'}$ are selected from 2-methylphenyl, 2-n-propylphenyl, 2-iso-propylphenyl, 2-iso-butylphenyl, 2-tert-butylphenyl, 2-fluorophenyl, 2-chlorophenyl, 2-bromophenyl, 4-methylphenyl, 4-n-propylphenyl, 4-iso-propylphenyl, 4-iso-butylphenyl, 4-tert-butylphenyl, 4-fluorophenyl, 4-chlorophenyl, 4-bromophenyl, 6-methylphenyl, 6-n-propylphenyl, 6-iso-propylphenyl, 6-iso-butylphenyl, 6-tert-butylphenyl, 6-fluorophenyl, 6-chlorophenyl, 6-bromophenyl, 2,6-dimethylphenyl, 2,6-di-n-propylphenyl, 2,6-di-iso-propylphenyl, 2,6-di-isobutylphenyl, 2,6-di-tert-butylphenyl, 2,6-difluorophenyl, 2,6-dichlorophenyl, 2,6-dibromophenyl, 2,4,6-trimethylphenyl, 2,4,6-tri-n-propylphenyl, 2,4,6-tri-iso-propylphenyl, 2,4,6-tri-iso-butylphenyl, 2,4,6-tri-tert-butylphenyl, 2,4,6-trifluorophenyl, 2,4,6-trichlorophenyl, 2,4,6-tribromophenyl, 2,3,4,5,6-pentafluorophenyl, 2,3,4,5,6-pentachlorophenyl, 2,3,4,5,6-pentabromophenyl, and the like.

In another embodiment of structures (XV), (XVI) and (XVII), X is independently selected from fluoride, chloride, bromide, methyl, ethyl, phenyl, benzyl, phenyloxy, benzloxy, 2-phenyl-2-propoxy, 1-phenyl-2-propoxy, 1-phenyl-2-butoxy, 2-phenyl-2-butoxy and the like.

As used herein, "chemically bonded combinations" means that adjacent groups may form a chemical bond between them, thus forming a ring system, either saturated, partially unsaturated, or aromatic.

Non-limiting examples of the Group 15-containing catalyst component are represented by the structures (XVIIIa)–(XVIIIf) (where "N" is nitrogen):

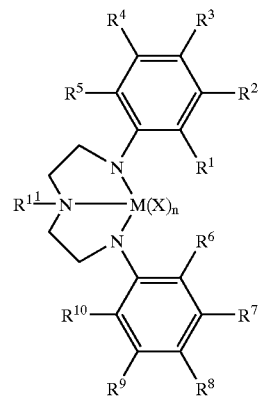
(XVIIIa)

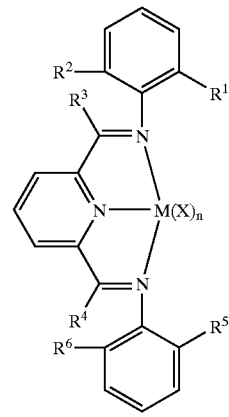
(XVIIIb)

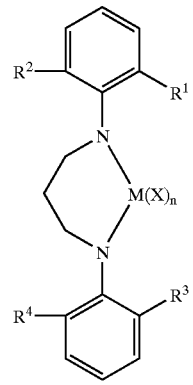
(XVIIIc)

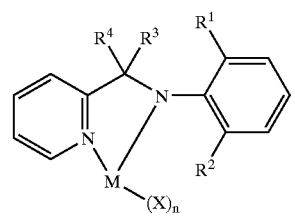
(XVIIId)

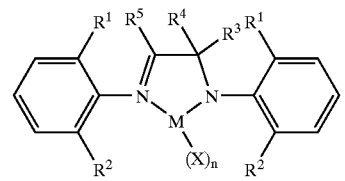
(XVIIIe)

-continued

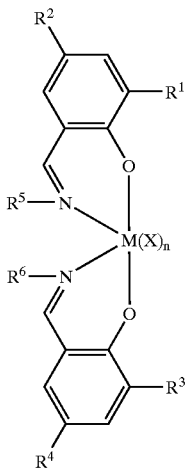

(XVIIIf)

wherein in structures (XVIIIa) through (XVIIIf) M is selected from Group 4 atoms in one embodiment; and M is selected from Zr and Hf in a more particular embodiment; and wherein $R^1$ through $R^{11}$ structures (XVIIIa) through (XVIIIf) are selected from hydride, fluorine radical, chlorine radical, bromine radical, methyl, ethyl, n-propyl, isopropyl, n-butyl, isobutyl, tert-butyl and phenyl; and X is selected from fluorine ion, chlorine ion, bromine ion, methyl, phenyl, benzyl, phenyloxy and benzyloxy; and n is an integer ranging from 0 to 4, and from 2 to 3 in a more particular embodiment.

The Group 15-containing catalyst components are prepared by methods known in the art, such as those disclosed in, for example, EP 0 893 454 A1, U.S. Pat. Nos. 5,889,128, 6,333,389 B2 and WO 00/37511.

The "Group 15-containing catalyst component" may comprise any combination of any "embodiment" described herein.

Phenoxide Transition Metal Catalyst Compositions

Phenoxide transition metal catalyst compositions are heteroatom substituted phenoxide ligated Group 3 to 10 transition metal or lanthanide metal compounds wherein the metal is bound to the oxygen of the phenoxide group. Phenoxide transition metal catalyst compounds may be represented by Formula XIX or XX:

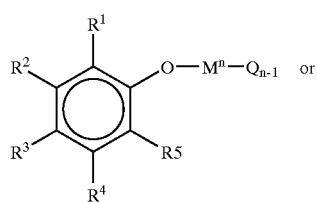

(XIX)

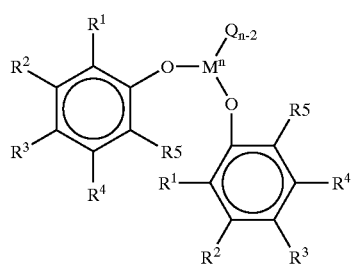

(XX)

wherein $R^1$ is hydrogen or a $C_4$ to $C_{100}$ group, preferably a tertiary alkyl group, preferably a $C_4$ to $C_{20}$ alkyl group, preferably a $C_4$ to $C_{20}$ tertiary alkyl group, preferably a neutral $C_4$ to $C_{100}$ group and may or may not also be bound to M;

at least one of $R^2$ to $R^5$ is a heteroatom containing group, the rest of $R^2$ to $R^5$ are independently hydrogen or a $C_1$ to $C_{100}$ group, preferably a $C_4$ to $C_{20}$ alkyl group, preferred examples of which include butyl, isobutyl, t-butyl, pentyl, hexyl, heptyl, isohexyl, octyl, isooctyl, decyl, nonyl, dodecyl, and any of $R^2$ to $R^5$ also may or may not be bound to M;

Each $R^1$ to $R^5$ group may be independently substituted or unsubstituted with other including heteroatoms or heteroatom containing group(s);

O is oxygen;

M is a Group 3 to Group 10 transition metal or lanthanide metal, preferably a Group 4 metal, preferably M is Ti, Zr or Hf;

n is the valence state of the metal M, preferably 2, 3, 4, or 5; and

Q is, and each Q may be independently be, an alkyl, halogen, benzyl, amide, carboxylate, carbamate, thiolate, hydride or alkoxide group, or a bond to an R group containing a heteroatom which may be any of $R^1$ to $R^5$.

A heteroatom containing group may be any heteroatom or a heteroatom bound to carbon, silicon or another heteroatom. Preferred heteroatoms include boron, aluminum, silicon, nitrogen, phosphorus, arsenic, tin, lead, antimony, oxygen, selenium, and tellurium. Particularly preferred heteroatoms include nitrogen, oxygen, phosphorus, and sulfur. Even more particularly preferred heteroatoms include nitrogen and oxygen. The heteroatom itself may be directly bound to the phenoxide ring or it may be bound to another atom or atoms that are bound to the phenoxide ring. The heteroatom containing group may contain one or more of the same or different heteroatoms. Preferred heteroatom containing groups include imines, amines, oxides, phosphines, ethers, ketones, oxoazolines heterocyclics, oxazolines, thioethers, and the like. Particularly preferred heteroatom containing groups include imines. Any two adjacent R groups may form a ring structure, preferably a 5 or 6 membered ring. Likewise the R groups may form multi-ring structures. In one embodiment any two or more R groups do not form a 5 membered ring.

In a preferred embodiment the heteroatom substituted phenoxide transition metal compound is an iminophenoxide Group 4 transition metal compound, and more preferably an iminophenoxidezirconium compound.

Supported Catalyst Systems

The activator and/or the polymerization catalyst compound may be combined with one or more support materials or carriers using any one of the support methods known in the art or as described below. In one embodiment the activator is in a supported form, for example deposited on, contacted with, vaporized with, bonded to, or incorporated within, adsorbed or absorbed in, or on, a support or carrier. In another embodiment, the activator and a catalyst compound may be deposited on, contacted with, vaporized with, bonded to, or incorporated within, adsorbed or absorbed in, or on, a support or carrier.

The terms "support" or "carrier" for purposes of this patent specification are used interchangeably and are any support material, preferably a porous support material, including inorganic or organic support materials. Non-limiting examples of inorganic support materials include inorganic oxides and inorganic chlorides. Other carriers include resinous support materials such as polystyrene, functionalized or crosslinked organic supports, such as polystyrene, divinyl benzene, polyolefins, or polymeric compounds, zeolites, talc, clays, or any other organic or inorganic support material and the like, or mixtures thereof.

In one embodiment, the heterocyclic compounds and the aluminum alkyl and/or the alumoxanes described above are combined with one or more support materials or carriers. In another embodiment the heterocyclic compound is combined with a support material, preferably silica, treated with the alkylaluminum or the alumoxane compound, such that the support has aluminum alkyl groups bonded thereto. The supported catalyst systems described herein may be prepared, generally, by the reaction of the heterocyclic compound with an aluminum alkyl or aluminoxane, the addition of the catalyst precursor, followed by addition of a support material such as silica or alumina.

The support materials utilized may be any of the conventional support materials. Preferably the supported material is a porous support material, for example, talc, inorganic oxides and inorganic chlorides. Other support materials include resinous support materials such as polystyrene, functionalized or crosslinked organic supports, such as polystyrene divinyl benzene polyolefins or polymeric compounds, zeolites, clays, or any other organic or inorganic support material and the like, or mixtures thereof.

The preferred support materials are inorganic oxides that include those Group 2, 3, 4, 5, 13 or 14 metal oxides. The preferred supports include silica, fumed silica, alumina, silica-alumina and mixtures thereof. Other useful supports include magnesia, titania, zirconia, magnesium chloride, montmorillonite, phyllosilicate, zeolites, talc, clays and the like. Also, combinations of these support materials may be used, for example, silica-chromium, silica-alumina, silica-titania and the like. Additional support materials may include those porous acrylic polymers. Other support materials include nanocomposites, aerogels, spherulites, and polymeric beads. Another support is fumed silica available under the trade name Cabosil™ TS-610, available from Cabot Corporation. Fumed silica is typically a silica with particles 7 to 30 nanometers in size that has been treated with dimethylsilyldichloride such that a majority of the surface hydroxyl groups are capped.

In another embodiment, any of the conventionally known inorganic oxides, such as silica, support materials that retain hydroxyl groups after dehydration treatment methods will be suitable in accordance with the invention. Because of availability, both of silica and silica containing metal oxide based supports, for example, silica-alumina, are preferred. Silica particles, gels and glass beads are most typical.

These metal oxide compositions may additionally contain oxides of other metals, such as those of Al, K, Mg, Na, Si, Ti and Zr and should preferably be treated by thermal and/or chemical means to remove water and free oxygen. Typically such treatment is in a vacuum in a heated oven, in a heated fluidized bed or with dehydrating agents such as organo silanes, siloxanes, alkyl aluminum compounds, etc. The level of treatment should be such that as much retained moisture and oxygen as is possible is removed, but that a chemically significant amount of hydroxyl functionality is retained. Thus calcining at up to 800° C. or more up to a point prior to decomposition of the support material, for several hours is permissible, and if higher loading of supported anionic activator is desired, lower calcining temperatures for lesser times will be suitable. Where the metal oxide is silica, loadings to achieve from less than 0.1 mmol to 3.0 mmol activator/g $SiO_2$ are typically suitable and can be achieved, for example, by varying the temperature of calcining from 200° C. to 1,000° C., such as from 300° C. to 900° C., 400° C. to 875° C., 500° C. to 850° C., 600° C. to 825° C., 700° C. to 800° C., and any combination of any limit with any lower limit.

The tailoring of hydroxyl groups available as attachment sites in this invention can also be accomplished by the pre-treatment with a less than stoichimetric amount of a chemical dehydrating agent. If calcining temperatures below 400° C. are employed, difunctional coupling agents (e.g., $(CH_3)_3SiCl_2$) may be employed to cap hydrogen bonded pairs of silanol groups which are present under the less severe calcining conditions. Similarly, use of the Lewis acid in excess of the stoichiometric amount needed for reaction with the transition metal compounds will serve to neutralize excess silanol groups without significant detrimental effect for catalyst preparation or subsequent polymerization.

In another embodiment, the support is a polymeric support, including hydroxyl-functional-group-containing polymeric substrates, but functional groups may be any of the primary alkyl amines, secondary alkyl amines, and others, where the groups are structurally incorporated in a polymeric chain and capable of a acid-base reaction with the Lewis acid such that a ligand filling one coordination site of the aluminum is protonated and replaced by the polymer incorporated functionality. See, for example, the functional group containing polymers of U.S. Pat. No. 5,288,677.

It is preferred that the support material, most preferably an inorganic oxide, has a surface area in the range of from about 10 to about 700 $m^2/g$, pore volume in the range of from about 0.1 to about 4.0 cc/g and average particle size in the range of from about 5 to about 500 μm. More preferably, the surface area of the support material is in the range of from about 50 to about 500 $m^2/g$, pore volume of from about 0.5 to about 3.5 cc/g and average particle size of from about 10 to about 200 μm. The average pore size of the carrier is typically in the range of from 10 to 1000 Å, preferably 50 to about 500 Å, and most preferably 75 to about 350 Å.

The support materials may be treated chemically, for example with a fluoride compound as described in WO 00/12565. Other supported activators are described in for example WO 00/13792 that refers to supported boron containing solid acid complex.

In one embodiment, the support material having an alkylaluminum and/or the alumoxane compound bonded thereto may be prepared by combining the aluminum containing compound with the support material in a suitable solvent. In one embodiment, the combining is carried out at any suitable pressure and temperature under an inert atmosphere. Preferably the combining is at atmospheric pressure, ambient temperature under nitrogen. More preferably the mixture is heated to less than about 200° C., more preferably less than 150° C. The reactants are contacted for a suitable about of time for example, for at least about 1 minute, preferably about 1 minute to about 10 hours, more preferably for about 1 minute to about 3 hours.

In another embodiment, an antistatic agent or surface modifier that is used in the preparation of the supported catalyst system as described in PCT publication WO 96/11960 may be used with catalyst systems including the activator compounds described herein. The catalyst systems may also be prepared in the presence of an olefin, for example 1-hexene.

In another embodiment, the activator and/or catalyst system may be combined with a carboxylic acid salt of a metal ester, for example aluminum carboxylates such as aluminum mono, di- and tri- stearates, aluminum octoates, oleates and cyclohexylbutyrates, as described in U.S. Pat. Nos. 6,300,436 and 6,306,984.

In another embodiment there is a method for producing a supported metallocene-type catalyst system, which may be used to support the activator described herein. In this method, the catalyst compound is slurried in a liquid to form a catalyst solution or emulsion. A separate solution is formed containing the activator. The liquid may be any compatible solvent or other liquid capable of forming a solution or the like with the catalyst compounds and/or activator. In the most preferred embodiment the liquid is a cyclic aliphatic or aromatic hydrocarbon, most preferably toluene. The catalyst compound and activator solutions are mixed together heated and added to a heated porous support or a heated porous support is added to the solutions such that the total volume of the metallocene-type catalyst compound solution and the activator solution or the metallocene-type catalyst compound and activator solution is less than four times the pore volume of the porous support, more preferably less than three times, even more preferably less than two times; preferred ranges being from 1.1 times to 3.5 times range and most preferably in the 1.2 to 3 times range.

In one embodiment, a method of forming a supported catalyst system, the amount of liquid, in which the activator described herein and/or a catalyst compound is present, is in an amount that is less than four times the pore volume of the support material, more preferably less than three times, even more preferably less than two times; preferred ranges being from 1.1 times to 3.5 times range and most preferably in the 1.2 to 3 times range. In an alternative embodiment, the amount of liquid in which the activator is present is from one to less than one times the pore volume of the support material utilized in forming the supported activator.

In one embodiment, the amount of heterocyclic nitrogen-containing compound ranges from 0.005 grams to 2.0 grams per gram of alkylaluminum treated silica. In another embodiment, the amount of heterocyclic nitrogen-containing compound ranges from 0.05 grams to 1.0 grams per gram of alkylaluminum treated silica. In yet another embodiment, the amount of heterocyclic nitrogen-containing compound ranges from 0.075 grams to 0.8 grams per gram of alkylaluminum treated silica.

Polymerization Process

The activators and catalysts described above, whether supported or not, are suitable for use in any prepolymerization and/or polymerization process over a wide range of temperatures and pressures. The temperatures may be in the range of from –60° C. to about 280° C., preferably from 50° C. to about 200° C. In one embodiment, the polymerization temperature is above 0° C., above 50° C., above 80° C., above 100° C., above 150° C., or above 200° C. In one embodiment, the pressures employed may be in the range from 1 atmosphere to about 500 atmospheres or higher.

Polymerization processes include solution, gas phase, slurry phase, and a high pressure process, or a combination thereof. Particularly preferred is a gas phase or slurry phase polymerization of one or more olefin(s) at least one of which is ethylene or propylene.

In one embodiment, the process is a solution, high pressure, slurry or gas phase polymerization process of one or more olefin monomers having from 2 to 30 carbon atoms, preferably 2 to 12 carbon atoms, and more preferably 2 to 8 carbon atoms. The invention is particularly well suited to the polymerization of two or more olefin monomers of ethylene, propylene, 1-butene, 1-pentene, 4-methyl-1-pentene, 1-hexene, 1-octene and 1-decene.

Other monomers useful in the process include ethylenically unsaturated monomers, diolefins having 4 to 18 carbon atoms, conjugated or nonconjugated dienes, polyenes, vinyl monomers and cyclic olefins. Non-limiting monomers useful in the invention may include norbornene, norbornadiene, isobutylene, isoprene, vinylbenzocyclobutane, styrenes, alkyl substituted styrene, ethylidene norbornene, dicyclopentadiene and cyclopentene.

In another embodiment, a copolymer of ethylene is produced, where with ethylene, a comonomer having at least one alpha-olefin having from 4 to 15 carbon atoms, preferably from 4 to 12 carbon atoms, and most preferably from 4 to 8 carbon atoms, is polymerized in a gas phase process.

In another embodiment, ethylene or propylene is polymerized with at least two different comonomers, optionally one of which may be a diene, to form a terpolymer.

In one embodiment, the invention is directed to a polymerization process, particularly a gas phase or slurry phase process, for polymerizing propylene alone or with one or more other monomers including ethylene, and/or other olefins having from 4 to 12 carbon atoms.

Typically in a gas phase polymerization process, a continuous cycle is employed where in one part of the cycle of a reactor system, a cycling gas stream, otherwise known as a recycle stream or fluidizing medium, is heated in the reactor by the heat of polymerization. This heat is removed from the recycle composition in another part of the cycle by a cooling system external to the reactor. Generally, in a gas fluidized bed process for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer.

The reactor pressure in a gas phase process may vary from about 100 psig (690 kPa) to about 500 psig (3448 kPa), preferably in the range of from about 200 psig (1379 kPa) to about 400 psig (2759 kPa), more preferably in the range of from about 250 psig (1724 kPa) to about 350 psig (2414 kPa).

The reactor temperature in a gas phase process may vary from about 30° C. to about 120° C., preferably from about 60° C. to about 115° C., more preferably in the range of from about 70° C. to about 110° C., and most preferably in the range of from about 70° C. to about 95° C. In another embodiment, the reactor temperature in a gas phase process is above 60° C.

Other gas phase processes include series or multistage polymerization processes. Also gas phase processes contemplated by the invention include those described in U.S. Pat. Nos. 5,627,242, 5,665,818 and 5,677,375, and European publications EP-A-0 794 200 EP-B1-0 649 992, EP-A-0 802 202 and EP-B-634 421.

In another embodiment, the process may produce greater than 500 lbs of polymer per hour (227 Kg/hr) to about 200,000 lbs/hr (90,900 Kg/hr) or higher of polymer, preferably greater than 1000 lbs/hr (455 Kg/hr), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700

Kg/hr) and most preferably greater than 65,000 lbs/hr (29,000 Kg/hr) to greater than 100,000 lbs/hr (45,500 Kg/hr).

A slurry polymerization process generally uses pressures in the range of from about 1 to about 50 atmospheres and even greater and temperatures in the range of 0° C. to about 120° C. In another embodiment, the slurry process temperature is above 100° C. In a slurry polymerization, a suspension of solid, particulate polymer is formed in a liquid polymerization diluent medium to which ethylene and comonomers and often hydrogen along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process must be operated above the reaction diluent critical temperature and pressure. Preferably, a hexane or an isobutane medium is employed.

In another embodiment, the polymerization technique is referred to as a particle form polymerization, or a slurry process where the temperature is kept below the temperature at which the polymer goes into solution. Such technique is well known in the art, and described in for instance U.S. Pat. No. 3,248,179 which is fully incorporated herein by reference. Other slurry processes include those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In another embodiment, the process may produce greater than 2000 lbs of polymer per hour (907 Kg/hr), more preferably greater than 5000 lbs/hr (2268 Kg/hr), and most preferably greater than 10,000 lbs/hr (4540 Kg/hr). In another embodiment the slurry reactor may produce greater than 15,000 lbs of polymer per hour (6804 Kg/hr), preferably greater than 25,000 lbs/hr (11,340 Kg/hr) to about 100,000 lbs/hr (45,500 Kg/hr).

Examples of solution processes are described in U.S. Pat. Nos. 4,271,060, 5,001,205, 5,236,998 and 5,589,555 and PCT WO 99/32525.

In one embodiment the slurry or gas phase process is operated in the presence of the catalyst system described herein and in the absence of or essentially free of any scavengers, such as triethylaluminum, trimethylaluminum, tri-isobutylaluminum and tri-n-hexylaluminum and diethyl aluminum chloride, dibutyl zinc and the like. This process is described in PCT publication WO 96/08520 and U.S. Pat. Nos. 5,712,352 and 5,763,543.

In another embodiment, the catalyst system may be injected into a reactor, particularly a gas phase reactor. In one embodiment the catalyst system is used in the unsupported form, preferably in a liquid form such as described in U.S. Pat. Nos. 5,317,036 and 5,693,727 and European publication EP-A-0 593 083. The polymerization catalyst in liquid form can be fed with an activator, and/or a support, and/or a supported activator together or separately to a reactor. The injection methods described in PCT publication WO 97/46599 may be utilized.

Where an unsupported catalyst system is used the mole ratio of the metal of the activator component to the metal of the catalyst compound is in the range of between 0.3:1 to 10,000:1, preferably 100:1 to 5000:1, and most preferably 500:1 to 2000:1.

Polymer Products

The polymers produced can be used in a wide variety of products and end-use applications. The polymers produced include linear low density polyethylene, elastomers, plastomers, high density polyethylenes, medium density polyethylenes, low density polyethylenes, polypropylene and polypropylene copolymers.

The polymers, typically ethylene based polymers, have a density in the range of from 0.86 g/cc to 0.97 g/cc, preferably in the range of from 0.88 g/cc to 0.965 g/cc, more preferably in the range of from 0.900 g/cc to 0.96 g/cc, even more preferably in the range of from 0.905 g/cc to 0.95 g/cc, yet even more preferably in the range from 0.910 g/cc to 0.940 g/cc, and most preferably greater than 0.915 g/cc, preferably greater than 0.920 g/cc, and most preferably greater than 0.925 g/cc. Density is measured in accordance with ASTM-D-1238.

The polymers produced typically have a molecular weight distribution, a weight average molecular weight to number average molecular weight ($M_w/M_n$) of greater than 1.5 to about 15, particularly greater than 2 to about 10, more preferably greater than about 2.2 to less than about 8, and most preferably from 2.5 to 8. The polymers may have a narrow molecular weight distribution and a broad composition distribution or vice-versa, and may be those polymers described in U.S. Pat. No. 5,798,427.

Also, the polymers typically have a narrow composition distribution as measured by Composition Distribution Breadth Index (CDBI). Further details of determining the CDBI of a copolymer are known to those skilled in the art. See, for example, PCT Patent Application WO 93/03093, published Feb. 18, 1993. The polymers in one embodiment have CDBI's generally in the range of greater than 50% to 100%, preferably 99%, preferably in the range of 55% to 85%, and more preferably 60% to 80%, even more preferably greater than 60%, still even more preferably greater than 65%. In another embodiment, polymers produced using a catalyst system described herein have a CDBI less than 50%, more preferably less than 40%, and most preferably less than 30%.

The polymers in one embodiment have a melt index (MI) or ($I_2$) as measured by ASTM-D-1238-E (190/2.16) in the range from no measurable flow to 1000 dg/min, more preferably from about 0.01 dg/min to about 100 dg/min, even more preferably from about 0.1 dg/min to about 50 dg/min, and most preferably from about 0.1 dg/min to about 10 dg/min.

In one embodiment, the polymers have a melt index ratio ($I_{21}/I_2$) ($I_{21}$ is measured by ASTM-D-1238-F) (190/21.6) of from 10 to less than 25, more preferably from about 15 to less than 25. The polymers, in a preferred embodiment, have a melt index ratio ($I_{21}/I_2$) of from greater than 25, more preferably greater than 30, even more preferably greater that 40, still even more preferably greater than 50 and most preferably greater than 65. For example, melt index ratio ($I_{21}/I_2$) may be of from 5 to 300, 10 to 200, 20 to 180, 30 to 160, 40 to 120, 50 to 100, 60 to 90, and a combination of any upper limit with any lower limit.

In yet another embodiment, propylene based polymers are produced. These polymers include atactic polypropylene, isotactic polypropylene, hemi-isotactic and syndiotactic polypropylene. Other propylene polymers include propylene block or impact copolymers. Propylene polymers of these types are well known in the art see for example U.S. Pat. Nos. 4,794,096, 3,248,455, 4,376,851, 5,036,034 and 5,459,117.

The polymers may be blended and/or coextruded with any other polymer. Non-limiting examples of other polymers include linear low density polyethylenes, elastomers, plastomers, high pressure low density polyethylene, high density polyethylenes, polypropylenes and the like.

The polymers produced and blends thereof are useful in such forming operations as film, sheet, and fiber extrusion and co-extrusion as well as blow molding, injection molding and rotary molding. Films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications. Fibers include melt spinning, solution spinning and melt blown fiber operations for use in woven or non-woven form to make filters, diaper fabrics, medical garments, geotextiles, etc. Extruded articles include medical tubing, wire and cable coatings, pipe, geomembranes, and pond liners. Molded articles include single and multi-layered constructions in the form of bottles, tanks, large hollow articles, rigid food containers and toys, etc.

EXAMPLES

In order to provide a better understanding, the following non-limiting examples are offered. In each of the examples to follow: indole, 4-bromoindole, 4-chloroindole, 4-fluoroindole, 5-fluoroindole, 7-bromoindole, 7-chloroindole, 7-bromoindole were purchased from Aldrich and used as received; anhydrous toluene and pentane were purchased from Aldrich and dried overnight over a sodium potassium alloy; 5-bromoindole, 5-chloroindole, 6-bromoindole, and 6-chloroindole were purchased form Biosynth Biochemica & Synthetica and used as received; (1,3-MeBuCp)$_2$ZrMe$_2$, 20 wt % solution in toluene was purchased from Norquay Single-Site Catalysts and used as received; and the silica was purchased from Grace Davison with a surface area of 546 m$^2$/g and a poor volume of 1.61 cc/g.

Example 1

In a 100 ml round bottom flask, 1.28 mmol of 4-bromoindole was dissolved in 30 mL of toluene. Triethylaluminum-treated silica (1.0 gram, Grace-Davison uncalcined silica titrated with triethylaluminum) was added to the solution. The flask was placed in an oil bath at 100° C. for three hours and stirred every half-hour. The flask was removed from the oil bath and allowed to cool to room temperature. The slurry was then filtered, washed with toluene, and partially dried under vacuum. In a dried 100 mL round bottom flask, 100 mg of (1,3-MeBuCp)$_2$ZrMe$_2$ (20 wt. % solution in toluene) was dissolved in 30 mL of toluene. The partially dried silica was transferred into the flask and the slurry was allowed to stand overnight at room temperature. The slurry was then filtered through a frit and dried under vacuum.

Example 2

In a 100 ml round bottom flask, 1.28 mmol of 4-chloroindole was dissolved in 30 mL of toluene. Triethylaluminum-treated silica (1.0 gram, Grace-Davison uncalcined silica titrated with triethylaluminum) was added to the solution. The flask was placed in an oil bath at 100° C. for three hours and stirred every half-hour. The flask was removed from the oil bath and allowed to cool to room temperature. The slurry was then filtered, washed with toluene, and partially dried under vacuum. In a dried 100 mL round bottom flask, 100 mg of (1,3-MeBuCp)$_2$ZrMe$_2$ (20 wt. % solution in toluene) was dissolved in 30 mL of toluene. The partially dried silica was transferred into the flask and the slurry was allowed to stand overnight at room temperature. The slurry was then filtered through a frit and dried under vacuum.

Example 3

In a 100 ml round bottom flask, 1.28 mmol of 4-fluoroindole was dissolved in 30 mL of toluene. Triethylaluminum-treated silica (1.0 gram, Grace-Davison uncalcined silica titrated with triethylaluminum) was added to the solution. The flask was placed in an oil bath at 100° C. for three hours and stirred every half-hour. The flask was removed from the oil bath and allowed to cool to room temperature. The slurry was then filtered, washed with toluene, and partially dried under vacuum. In a dried 100 mL round bottom flask, 100 mg of (1,3-MeBuCp)$_2$ZrMe$_2$ (20 wt. % solution in toluene) was dissolved in 30 mL of toluene. The partially dried silica was transferred into the flask and the slurry was allowed to stand overnight at room temperature. The slurry was then filtered through a frit and dried under vacuum.

Example 4

In a 100 ml round bottom flask, 1.28 mmol of 5-bromoindole was dissolved in 30 mL of toluene. Triethylaluminum-treated silica (1.0 gram, Grace-Davison uncalcined silica titrated with triethylaluminum) was added to the solution. The flask was placed in an oil bath at 100° C. for three hours and stirred every half-hour. The flask was removed from the oil bath and allowed to cool to room temperature. The slurry was then filtered, washed with toluene, and partially dried under vacuum. In a dried 100 mL round bottom flask, 100 mg of (1,3-MeBuCp)$_2$ZrMe$_2$ (20 wt. % solution in toluene) was dissolved in 30 mL of toluene. The partially dried silica was transferred into the flask and the slurry was allowed to stand overnight at room temperature. The slurry was then filtered through a frit and dried under vacuum.

Example 5

In a 100 ml round bottom flask, 1.28 mmol of 5-chloroindole was dissolved in 30 mL of toluene. Triethylaluminum-treated silica (1.0 gram, Grace-Davison uncalcined silica titrated with triethylaluminum) was added to the solution. The flask was placed in an oil bath at 100° C. for three hours and stirred every half-hour. The flask was removed from the oil bath and allowed to cool to room temperature. The slurry was then filtered, washed with toluene, and partially dried under vacuum. In a dried 100 mL round bottom flask, 100 mg of (1,3-MeBuCp)$_2$ZrMe$_2$ (20 wt. % solution in toluene) was dissolved in 30 mL of toluene. The partially dried silica was transferred into the flask and the slurry was allowed to stand overnight at room temperature. The slurry was then filtered through a frit and dried under vacuum.

Example 6

In a 100 ml round bottom flask, 1.28 mmol of 5-chloroindole was dissolved in 30 mL of toluene. Triethylaluminum-treated silica (1.0 gram, Grace-Davison uncalcined silica titrated with triethylaluminum) was added to the solution. The flask was placed in an oil bath at 100° C. for three hours and stirred every half-hour. The flask was removed from the oil bath and allowed to cool to room temperature. The slurry was then filtered, washed with toluene, and partially dried under vacuum. In a dried 100 mL round bottom flask, 100 mg of $(1,3-MeBuCp)_2ZrMe_2$ (20 wt. % solution in toluene) was dissolved in 30 mL of toluene. The partially dried silica was transferred into the flask and the slurry was allowed to stand overnight at room temperature. The slurry was then filtered through a frit and dried under vacuum.

Example 7

In a 100 ml round bottom flask, 1.28 mmol of 6-bromoindole was dissolved in 30 mL of toluene. Triethylaluminum-treated silica (1.0 gram, Grace-Davison uncalcined silica titrated with triethylaluminum) was added to the solution. The flask was placed in an oil bath at 100° C. for three hours and stirred every half-hour. The flask was removed from the oil bath and allowed to cool to room temperature. The slurry was then filtered, washed with toluene, and partially dried under vacuum. In a dried 100 mL round bottom flask, 100 mg of $(1,3-MeBuCp)_2ZrMe_2$ (20 wt. % solution in toluene) was dissolved in 30 mL of toluene. The partially dried silica was transferred into the flask and the slurry was allowed to stand overnight at room temperature. The slurry was then filtered through a frit and dried under vacuum.

Example 8

In a 100 ml round bottom flask, 1.28 mmol of 6-chloroindole was dissolved in 30 mL of toluene. Triethylaluminum-treated silica (1.0 gram, Grace-Davison uncalcined silica titrated with triethylaluminum) was added to the solution. The flask was placed in an oil bath at 100° C. for three hours and stirred every half-hour. The flask was removed from the oil bath and allowed to cool to room temperature. The slurry was then filtered, washed with toluene, and partially dried under vacuum. In a dried 100 mL round bottom flask, 100 mg of $(1,3-MeBuCp)_2ZrMe_2$ (20 wt. % solution in toluene) was dissolved in 30 mL of toluene. The partially dried silica was transferred into the flask and the slurry was allowed to stand overnight at room temperature. The slurry was then filtered through a frit and dried under vacuum.

Example 9

In a 100 ml round bottom flask, 1.28 mmol of 6-fluoroindole was dissolved in 30 mL of toluene. Triethylaluminum-treated silica (1.0 gram, Grace-Davison uncalcined silica titrated with triethylaluminum) was added to the solution. The flask was placed in an oil bath at 100° C. for three hours and stirred every half-hour. The flask was removed from the oil bath and allowed to cool to room temperature. The slurry was then filtered, washed with toluene, and partially dried under vacuum. In a dried 100 mL round bottom flask, 100 mg of $(1,3-MeBuCp)_2ZrMe_2$ (20 wt. % solution in toluene) was dissolved in 30 mL of toluene. The partially dried silica was transferred into the flask and the slurry was allowed to stand overnight at room temperature. The slurry was then filtered through a frit and dried under vacuum.

Example 10

In a 100 ml round bottom flask, 1.28 mmol of 7-bromoindole was dissolved in 30 mL of toluene. Triethylaluminum-treated silica (1.0 gram, Grace-Davison uncalcined silica titrated with triethylaluminum) was added to the solution. The flask was placed in an oil bath at 100° C. for three hours and stirred every half-hour. The flask was removed from the oil bath and allowed to cool to room temperature. The slurry was then filtered, washed with toluene, and partially dried under vacuum. In a dried 100 mL round bottom flask, 100 mg of $(1,3-MeBuCp)_2ZrMe_2$ (20 wt. % solution in toluene) was dissolved in 30 mL of toluene. The partially dried silica was transferred into the flask and the slurry was allowed to stand overnight at room temperature. The slurry was then filtered through a frit and dried under vacuum.

Example 11

In a 100 ml round bottom flask, 1.28 mmol of 7-chloroindole was dissolved in 30 mL of toluene. Triethylaluminum-treated silica (1.0 gram, Grace-Davison uncalcined silica titrated with triethylaluminum) was added to the solution. The flask was placed in an oil bath at 100° C. for three hours and stirred every half-hour. The flask was removed from the oil bath and allowed to cool to room temperature. The slurry was then filtered, washed with toluene, and partially dried under vacuum. In a dried 100 mL round bottom flask, 100 mg of $(1,3-MeBuCp)_2ZrMe_2$ (20 wt. % solution in toluene) was dissolved in 30 mL of toluene. The partially dried silica was transferred into the flask and the slurry was allowed to stand overnight at room temperature. The slurry was then filtered through a frit and dried under vacuum.

Example 12

In a 100 ml round bottom flask, 1.28 mmol of 7-fluorindole was dissolved in 30 mL of toluene. Triethylaluminum-treated silica (1.0 gram, Grace-Davison uncalcined silica titrated with triethylaluminum) was added to the solution. The flask was placed in an oil bath at 100° C. for three hours and stirred every half-hour. The flask was removed from the oil bath and allowed to cool to room temperature. The slurry was then filtered, washed with toluene, and partially dried under vacuum. In a dried 100 mL round bottom flask, 100 mg of $(1,3-MeBuCp_2ZrMe_2)$ (20 wt. % solution in toluene) was dissolved in 30 mL of toluene. The partially dried silica was transferred into the flask and the slurry was allowed to stand overnight at room temperature. The slurry was then filtered through a frit and dried under vacuum.

Example 13

In a 100 ml round bottom flask, 1.28 mmol of 5,6-dichloroindole was dissolved in 30 mL of toluene. Triethylaluminum-treated silica (1.0 gram, Grace-Davison uncalcined silica titrated with triethylaluminum) was added to the solution. The flask was placed in an oil bath at 100° C. for three hours and stirred every half hour. The flask was removed from the oil bath and allowed to cool to room temperature. The slurry was then filtered, washed with toluene, and partially dried under vacuum. In a dried 100 mL round bottom flask, 100 mg of (1,3-MeBuCp$_2$ZrMe$_2$) (20 wt. % solution in toluene) was dissolved in 30 mL of toluene. The partially dried silica was transferred into the flask and the slurry was allowed to stand overnight at room temperature. The slurry was then filtered through a frit and dried under vacuum.

Comparative Example 1

In a 100 ml round bottom flask, 1.28 mmol of indole was dissolved in 30 mL of toluene. Triethylaluminum-treated silica (1.0 gram, Grace-Davison uncalcined silica titrated with triethylaluminum) was added to the solution. The flask was placed in an oil bath at 100° C. for three hours and stirred every half-hour. The flask was removed from the oil bath and allowed to cool to room temperature. The slurry was then filtered, washed with toluene, and partially dried under vacuum. In a dried 100 mL round bottom flask, 100 mg of (1,3-MeBuCp$_2$ZrMe$_2$) (20 wt. % solution in toluene) was dissolved in 30 mL of toluene. The partially dried silica was transferred into the flask and the slurry was allowed to stand overnight at room temperature. The slurry was then filtered through a frit and dried under vacuum.

Polymerizations

In each of the Examples above, polymerizations were performed in a 1 liter lab Autoclave reactor using 25 mg of supported catalyst, 30 mL of 1-hexene, 0.7 mL of tri-n-octylaluminum (25 wt % solution in hexane), 400 mL of isobutane and an ethylene partial pressure of 130 Psi. Polymerizations were performed at 85° C. for 40 minutes. After the reactor cooled downed and depressurized, hexane (300 mL) was used to wash the polymer out of the reactor body and into a crystallization dish. The polymer was then vacuum filtered using a glass frit funnel and washed with 100 mL of hexane. The resulting powder was air dried overnight and weighed. The activity of the catalysts was also calculated. The activity is the grams of polymer per grams of catalyst per hour. Table 1 below summarizes these results.

TABLE 1

| Activator | Supported Catalyst (mgs) | Yield (grams) | Activity (g of polymer) per (g Cat./(hr)) |
| --- | --- | --- | --- |
| EX 1: | 25 | 12.5 | 750 |
| 4-Bromoindole | 25 | 15.6 | 936 |
| | average | 14.05 | 843 |
| | std. dev. | 2.19 | 132 |
| EX 2: | 25 | 17.5 | 1050 |
| 4-Chloroindole | 25 | 16.5 | 966 |
| | average | 17.00 | 1008 |
| | std. dev. | 0.71 | 59.5 |
| EX 3: | 25 | 15.5 | 930 |
| 4-Fluoroindole | 25 | 14.3 | 858 |
| | average | 14.90 | 894 |
| | std. dev. | 0.85 | 51.0 |
| EX 4: | 25 | 24.1 | 1446 |
| 5-Bromoindole | 25 | 24.3 | 1458 |
| | average | 24.20 | 1452 |
| | std. dev. | 0.14 | 8.49 |
| EX 5: | 25 | 23.6 | 1416 |
| 5-Chloroindole | 25 | 26.4 | 1584 |
| | average | 25.00 | 1500 |
| | std. dev. | 1.98 | 118.8 |
| EX 6: | 25 | 18.8 | 1128 |
| 5-Fluoroindole | 25 | 18.8 | 1074 |
| | average | 18.80 | 1101 |
| | std. dev. | 0.00 | 38.0 |

TABLE 1-continued

| Activator | Supported Catalyst (mgs) | Yield (grams) | Activity (g of polymer) per (g Cat./(hr)) |
| --- | --- | --- | --- |
| EX 7: | 25 | 23.8 | 1428 |
| 6-Bromoindole | 25 | 20.6 | 1236 |
| | average | 22.20 | 1332 |
| | std. dev. | 2.26 | 135.8 |
| EX 8: | 25 | 20.3 | 1218 |
| 6-Chloroindole | 25 | 23 | 1380 |
| | average | 21.65 | 1299 |
| | std. dev. | 1.91 | 114.6 |
| EX 9: | 25 | 11.6 | 696 |
| 6-Fluoroindole | 25 | 12.2 | 732 |
| | average | 11.90 | 714 |
| | std. dev. | 0.42 | 25.5 |
| EX 10: | 25 | 2 | 120 |
| 7-Bromoindole | 25 | 2 | 120 |
| | average | 2.00 | 120 |
| | std. dev. | 0.00 | 0.00 |
| EX 11: | 25 | 3.1 | 186 |
| 7-Chloroindole | 25 | 4 | 240 |
| | average | 3.55 | 213 |
| | std. dev. | 0.64 | 38.2 |
| EX 12: | 25 | 10.7 | 642 |
| 7-Fluoroindole | 25 | 11.8 | 708 |
| | average | 11.25 | 675 |
| | std. dev. | 0.78 | 46.7 |
| EX 13: | 25 | 45.6 | 2736 |
| 5,6-dichloroindole | 25 | 47.5 | 2850 |
| | average | 46.55 | 2793 |
| | std. dev. | 1.34 | 80.6 |
| Comparative | 25 | 5.8 | 331 |
| EX 1: Indole | 25 | 6.7 | 365 |
| | average | 6.25 | 348 |
| | std. dev. | 0.64 | 24 |

The 4-halo-indoles, 5-halo-indoles and 6-halo-indoles, each showed between 2 times and 4 times the catalyst activity compared to the non-halogenated indole, as shown in Table 1. However, it was surprisingly discovered that the 5-halo-indoles and the 6-halo-indoles provided up to 72% more activity compared to the 4-halo-indoles and up to 12 times the activity of the 7-halo-indoles. It was also surprisingly discovered that the 5-halo-indoles provided between 9% and 54% more activity than the respective 6-halo-indoles.

Unless otherwise indicated, all numbers expressing quantities of ingredients, properties, reaction conditions, and so forth, used in the specification and claims are to be understood as approximations based on the desired properties sought to be obtained by the present invention, and the error of measurement, etc., and should at least be construed in light of the number of reported significant digits and by applying ordinary rounding techniques. Notwithstanding that the numerical ranges and values setting forth the broad scope of the invention are approximations, the numerical values set forth are reported as precisely as possible.

All priority documents are herein fully incorporated by reference for all jurisdictions in which such incorporation is permitted. Further, all documents cited herein, including testing procedures, are herein fully incorporated by reference for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A catalyst system comprising:
one or more polymerization catalysts selected from the group consisting of metallocenes; and
an activator comprising one or more heterocyclic nitrogen-containing ligands coordinated to a Group 13 atom, wherein the activator is a reaction product of one or more alkyl substituted Group 13 atom-containing compounds and one or more heterocyclic nitrogen-containing compounds, the one or more heterocyclic nitrogen-containing ligands represented by:

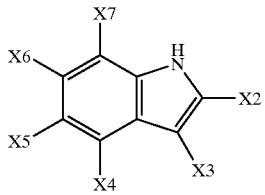

wherein each substituent X2, X3, X4, X5, X6, and X7 is independently selected from the group consisting of hydrogen, chlorine, fluorine, iodine, and bromine.

2. The catalyst system of claim 1, wherein X4 is chlorine, fluorine, iodine, or bromine and X2, X3, X5, X6, and X7 are hydrogen.

3. The catalyst system of claim 1, wherein X5 is chlorine, fluorine, iodine, or bromine and X2, X3, X4, X6, and X7 are hydrogen.

4. The catalyst system of claim 1, wherein X6 is chlorine, fluorine, iodine, or bromine and X2, X3, X4, X5, and X7 are hydrogen.

5. The catalyst system of claim 1, wherein both X4 and X5 is chlorine, fluorine, iodine, or bromine and X2, X3, X6, and X7 are hydrogen.

6. The catalyst system of claim 1, wherein both X5 and X6 are chlorine, fluorine, iodine, or bromine, and X2, X3, X4 and X7 are hydrogen.

7. The catalyst system of claim 1, wherein the heterocyclic nitrogen-containing ligand is selected from the group consisting of 4-bromoindole, 4-chloroindole, 4-fluoroindole, 5-bromoindole, 5-chloroindole, 5-fluoroindole, 4,5,6,7-tetrafluoroindole, 2-methylindole, and 3-methylindole.

8. The catalyst system of claim 1, wherein the Group 13 atom is aluminum.

9. The catalyst system of claim 1, wherein the Group 13 atom is boron.

10. The catalyst system of claim 1, further comprising a support material.

11. The catalyst system of claim 1, further comprising a support material that comprises silica.

12. The catalyst system of claim 1, further comprising a support material treated with an aluminoxane or an alkyl aluminum compound such that the support comprises aluminum alkyl groups bonded thereto.

13. A catalyst system comprising:
one or more polymerization catalysts selected from the group consisting of metallocenes; and
an activator comprising one or more heterocyclic nitrogen-containing ligands coordinated to an aluminum atom, wherein the activator is a reaction product of one or more alkyl substituted aluminum-containing compounds and one or more heterocyclic nitrogen-containing compounds, the one or more heterocyclic nitrogen-containing ligands represented by:

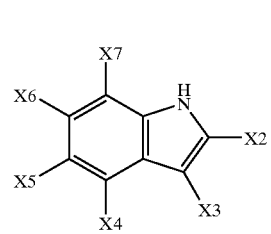

wherein each substituent X2, X3, X4, X5, X6, and X7 is independently selected from the group consisting of hydrogen, chlorine, fluorine, iodine, and bromine.

14. The catalyst system of claim 13, wherein each substituent X2, X3, X4, and X7 is hydrogen and X5 and X6 are independently selected from the group consisting of hydrogen, chlorine, fluorine, iodine, and bromine.

15. The catalyst system of claim 13, further comprising a support material treated with an aluminoxane or an alkyl aluminum compound such that the support comprises aluminum alkyl groups bonded thereto.

16. A catalyst system comprising:
one or more polymerization catalysts selected from the group consisting of metallocenes;
at least one activator; and
a support material treated with an aluminoxane or an alkyl aluminum compound such that the support comprises aluminum alkyl groups bonded thereto;
wherein the activator is represented by one of the following formulas:

$$(R'_xM(JY)_y)_n \qquad (a)$$

$$[((JY)_yR'_x)_nM-O-M((R'_x(JY)_y)_n]_m \qquad (b)$$

$$(OMR'_x(JY)_y)_n \qquad (c)$$

wherein M is aluminum, O is oxygen, and (JY) is a heterocyclic nitrogen-containing ligand represented by:

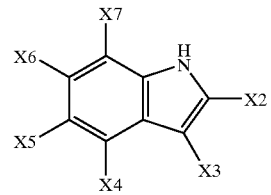

wherein each substituent X2, X3, X4, X5, X6, and X7 is independently selected from the group consisting of hydrogen, chlorine, fluorine, iodine, and bromine;
wherein n is 1 or 2 in formula (a); n is 2 in formula (b); and n is an number from 1 to 1,000 in formula (c);
wherein m is a number from 1 to 10;
wherein x+y=the valence of M in formula (a); x+y=the valence of M−1 in formula (b); and x+y=valence of M−2 in formula (c); and
wherein each R' is a substituent group bonded to M.

17. The catalyst system of claim 16, wherein each substituent X2, X3, X4 and X7 is hydrogen, and X5 and X6 are independently selected from the group consisting of hydrogen, chlorine, fluorine, iodine, and bromine.

18. The catalyst system of claim 16, wherein each R' is independently selected from the group consisting of methyl, ethyl, propyl, butyl, pentyl, hexyl, cyclopentyl, cyclohexyl, and isomers thereof.

19. The catalyst system of claim 16, wherein each R' is bonded to the support material.

* * * * *